United States Patent
Segawa

(10) Patent No.: US 9,538,906 B2
(45) Date of Patent: Jan. 10, 2017

(54) CAPSULE-TYPE MEDICAL APPARATUS AND METHOD OF MANUFACTURING CAPSULE-TYPE MEDICAL APPARATUS

(71) Applicant: OLYMPUS CORPORATION, Tokyo (JP)

(72) Inventor: Hidetake Segawa, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 744 days.

(21) Appl. No.: 13/711,669

(22) Filed: Dec. 12, 2012

(65) Prior Publication Data

US 2013/0102845 A1   Apr. 25, 2013

Related U.S. Application Data

(62) Division of application No. 12/115,894, filed on May 6, 2008, now Pat. No. 8,353,821.

(30) Foreign Application Priority Data

May 8, 2007 (JP) ................................. 2007-123817

(51) Int. Cl.
   *A61B 1/00* (2006.01)
   *A61B 1/04* (2006.01)
   (Continued)

(52) U.S. Cl.
   CPC ............. *A61B 1/041* (2013.01); *A61B 1/0011* (2013.01); *A61B 1/00071* (2013.01);
   (Continued)

(58) Field of Classification Search
   USPC ........................................................ 600/128
   See application file for complete search history.

(56) References Cited

U.S. PATENT DOCUMENTS

2003/0029558 A1\* 2/2003 Hochrainer et al. ........ 156/272.8
2005/0043583 A1\* 2/2005 Killmann et al. ............ 600/109
(Continued)

FOREIGN PATENT DOCUMENTS

AU   2006233956 A1   10/2006
JP   8-503384 A   4/1996
(Continued)

OTHER PUBLICATIONS

Notice of Rejection dated Feb. 19, 2013 from corresponding Japanese Patent application No. 2007-123817 together with an English language translation.

(Continued)

*Primary Examiner* — Matthew J. Kasztejna
*Assistant Examiner* — Rynae Boler
(74) *Attorney, Agent, or Firm* — Scully, Scott, Murphy & Presser, PC

(57) ABSTRACT

The present invention provides a capsule-type medical apparatus and a method of manufacturing a capsule-type medical apparatus which can prevent a contact between a burr formed on an optical dome which is a part of a capsule-like casing and a living body in a subject. The capsule-type medical apparatus has a capsule-like casing which can be introduced inside the subject. The casing is configured with optically transparent optical domes and a cylindrical trunk member having an outer diameter dimension larger than an outer diameter dimension of the optical domes. The cylindrical trunk member is fitted onto an outer circumferential surface of the optical domes so as to cover each of the optical domes up to a portion near the burr formed thereon. The cylindrical trunk member has a step higher than the burr so as to prevent a contact between the burr and a living body in the subject.

6 Claims, 11 Drawing Sheets

(51) Int. Cl.
 *A61B 5/00* (2006.01)
 *A61B 5/07* (2006.01)
 *H04N 5/225* (2006.01)

(52) U.S. Cl.
 CPC ............ *A61B 1/00181* (2013.01); *A61B 5/07* (2013.01); *A61B 5/6861* (2013.01); *A61B 2562/12* (2013.01); *H04N 2005/2255* (2013.01)

(56) References Cited

U.S. PATENT DOCUMENTS

| | | | |
|---|---|---|---|
| 2005/0049461 A1* | 3/2005 | Honda et al. | 600/109 |
| 2006/0235276 A1* | 10/2006 | Takase et al. | 600/177 |
| 2007/0118017 A1* | 5/2007 | Honda | 600/160 |
| 2007/0191683 A1 | 8/2007 | Fujimori | |
| 2007/0197870 A1 | 8/2007 | Uchiyama et al. | |

FOREIGN PATENT DOCUMENTS

| | | |
|---|---|---|
| JP | 2003-93367 A | 4/2003 |
| JP | 2003-210393 A | 7/2003 |
| JP | 2004-522467 | 7/2004 |
| JP | 2005-198964 | 7/2005 |
| JP | 2005-204924 | 8/2005 |
| JP | 2005-328998 A | 12/2005 |
| JP | 2006-297 A | 1/2006 |
| JP | 2006-42900 A | 2/2006 |
| JP | 2006-141725 A | 6/2006 |
| JP | 2007-068894 | 3/2007 |
| JP | 2007-075162 | 3/2007 |
| WO | 94/01165 A1 | 1/1994 |
| WO | WO 02/36007 A1 | 5/2002 |

OTHER PUBLICATIONS

Non-Final U.S. Office Action dated Apr. 3, 2012 issued in corresponding U.S. Appl. No. 12/115,894.
Notice of Allowance and Fee(s) Due dated Sep. 14, 2012 issued in corresponding U.S. Appl. No. 12/115,894.
Decision of a Patent Grant dated Jul. 16, 2013 from corresponding Japanese Patent Application No. 2007-123817, together with an English language translation.
Extended Supplementary European Search Report dated Apr. 16, 2014 issued in corresponding Application No./ Patent No. 08740064.4-1657 / 2143367 PCT/JP2008056961.

* cited by examiner

CAPSULE-TYPE MEDICAL APPARATUS AND METHOD OF MANUFACTURING CAPSULE-TYPE MEDICAL APPARATUS

CROSS-REFERENCE TO RELATED APPLICATIONS

This application is a Divisional Application of U.S. Ser. No. 12/115,894 filed May 6, 2008, which is based upon and claims the benefit of priority from Japanese Patent Application No. 2007-123817, filed May 8, 2007, the entire contents of each of which are incorporated herein by reference.

BACKGROUND OF THE INVENTION

1. Field of the Invention

The present invention relates to a capsule-type medical apparatus, which is introduced into an inside of an internal organ of a subject such as a patient to acquire in-vivo information of the subject, and a method of manufacturing such a capsule-type medical apparatus.

2. Description of the Related Art

Conventionally, a swallowable capsule endoscope having an imaging function and a radio communication function appears in the field of endoscope. The capsule endoscope is introduced into an internal organ of a subject such as a patient for an observation (examination) of an inside of the internal organ. For example, the subject swallows the capsule endoscope from the mouth. Thereafter, the capsule endoscope moves through inside the internal organs following peristaltic movements and the like while sequentially picking up an image of the inside of the subject (hereinafter may referred to as "intra-body image") at a predetermined interval, for example, at an interval of 0.5 second. Eventually, the capsule endoscope is naturally excreted outside the body of the subject.

While the capsule endoscope is in the internal organs of the subject, the intra-body images picked up by the capsule endoscope are sequentially transmitted from the capsule endoscope to a receiver outside the body by radio communication. The subject carries the receiver, and the receiver receives the intra-body images radio transmitted from the capsule endoscope introduced inside the internal organs of the subject and stores the received intra-body images in a recording medium.

The intra-body images stored in the recording medium of the receiver are taken into an image display device such as workstation. The image display device displays the intra-body images of the subject acquired via the recording medium. Doctors, nurses, and the like can make diagnosis of the subject by observing the intra-body images displayed by the image display device.

The capsule endoscope as described above has a capsule-like casing including a transparent optical dome and a cylindrical trunk member having an open end where the transparent optical dome is attached. Inside the capsule-like casing, an illuminating unit such as an LED (light emitting diode) illuminating the inside of the internal organ through the optical dome, an optical unit such as a lens that collects light reflected from the inside of the internal organ illuminated by the illuminating unit, and an imaging unit such as a CCD (charge-coupled device) that picks up an image of the inside of the internal organ (i.e., intra-body image) formed by the optical unit are provided (see, for example, Japanese Patent Application Laid-Open No. 2005-198964, and Japanese Patent Application Laid-Open No. 2005-204924).

The optical dome of the capsule-like casing mentioned above includes a cylindrical portion fitted to the open end of the cylindrical trunk member and a dome portion having a dome-like shape. Illuminating light emitted from the illuminating unit inside the capsule-like casing passes through the dome portion to illuminate the inside of the internal organ, whereas reflected light from the inside of the internal organ thus illuminated passes through the dome portion and reaches the optical unit. Hence, mirror finish is applied to an outer wall surface and inner wall surface of the dome portion which transmits the illuminating light and the reflected light. A mold employed for molding the optical dome is divided into a mold part for molding the dome portion for which the mirror finish is required, and a mold part for molding the cylindrical portion. When the mold for the optical dome is divided into a dome-portion-side mold part and a cylindrical-portion-side mold part, the mirror finish of a semispherical concave surface (concave surface for forming the outer wall surface of the dome portion) of the dome-portion-side mold part can be performed easily.

However, when the optical dome is molded by the mold as mentioned above, burrs are often formed on the outer wall surface of the optical dome along a boundary line (hereinafter referred to as "parting line") between the dome-portion-side mold part and the cylindrical-portion-side mold part. When the optical dome on whose outer wall surface such a burr is formed is employed in the capsule endoscope, the burr of the optical dome comes into contact with a living body such as an inner wall of the internal organ during the travel of the capsule endoscope in the internal organ of the subject.

SUMMARY OF THE INVENTION

An object of the present invention is to at least solve the problem described above.

A capsule-type medical apparatus according to one aspect of the present invention includes a capsule-like casing that can be introduced inside a subject, an optical dome that forms a transparent portion of the capsule-like casing, and a cylindrical trunk member that forms a trunk portion of the capsule-like casing, the cylindrical trunk member being fitted onto an outer circumferential surface of the optical dome and preventing a contact between a living body in the subject and a burr formed on the optical dome.

A method of manufacturing a capsule-type medical apparatus according to another aspect of the present invention is a method of manufacturing a capsule-type medical apparatus including a capsule-like casing which can be introduced inside a subject and is configured with an optical dome and a cylindrical trunk member, and the method includes firstly applying a mirror finish to a mold part for molding an outer wall surface of an optically transparent dome portion which is a part of the optical dome, combining a mold part for molding an outer wall surface of a cylindrical portion which is a remaining portion of the optical dome and on whose outer circumferential surface the cylindrical trunk member is fitted and a mold part to which the mirror finish is applied in the firstly applying, secondly applying a mirror finish on a mold part for molding an inner wall surface of the dome portion, and molding the optical dome by the mold parts combined in the combining and the mold part to which the mirror finish is applied in the secondly applying, and forming a burr on a boundary between the outer wall surface of the dome portion and the outer wall surface of the cylindrical portion.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Exemplary embodiments of a capsule-type medical apparatus and a method of manufacturing the capsule-type medical apparatus according to the present invention will be described in detail below with reference to the accompanying drawings. In the following description of the embodiments, a capsule endoscope which is introduced into an inside of the subject and which has an imaging function for picking up an intra-body image which is an example of in-vivo information of the subject and a radio communication function for radio transmitting the picked-up intra-body image is described as an example of the capsule-type medical apparatus of the present invention, though the present invention is not limited by the embodiments.

First Embodiment

Figure 1:
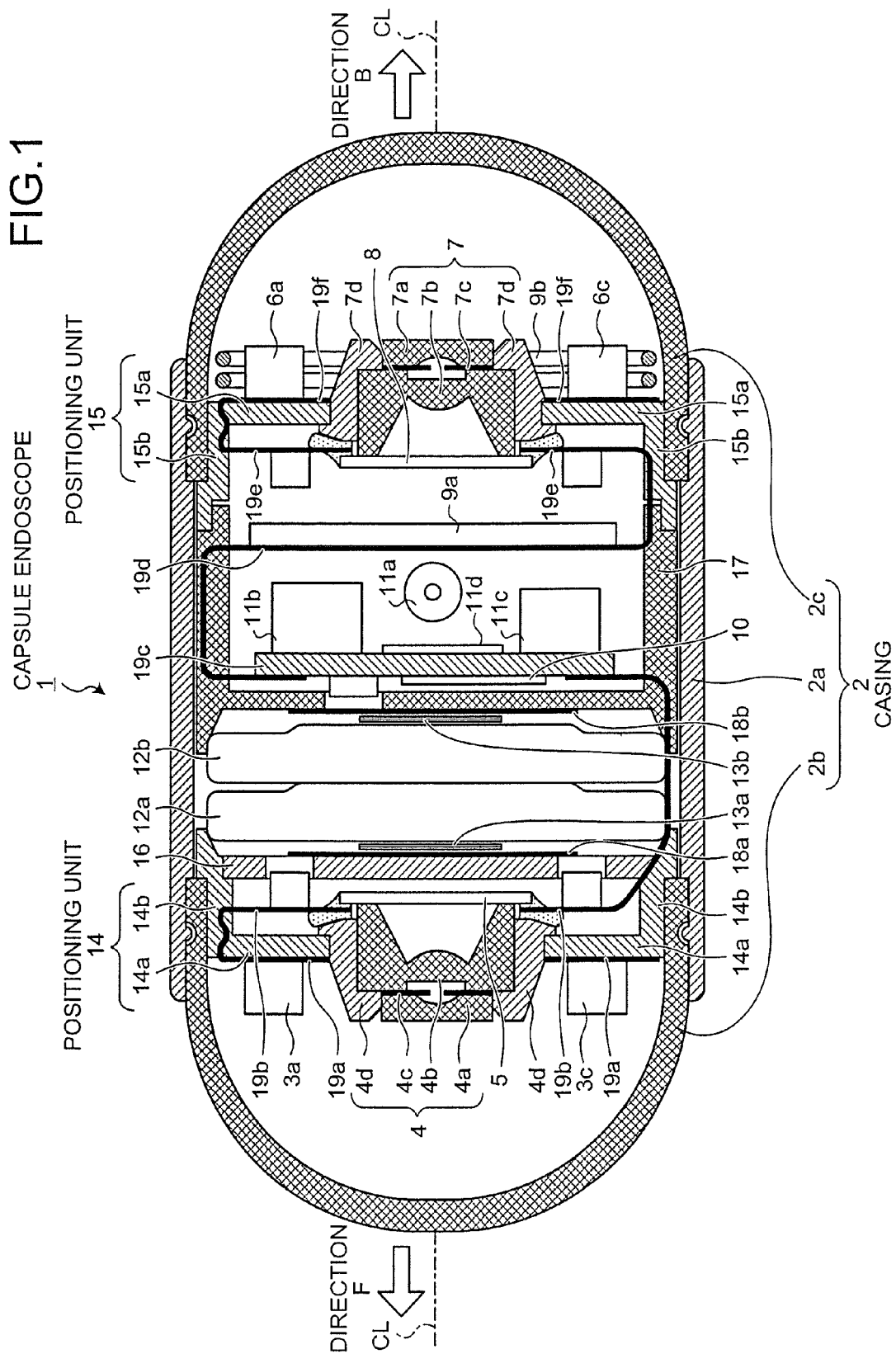
FIG. 1 is a schematic vertical sectional view of one configuration example of a capsule endoscope according to a first embodiment of the present invention.
Figure 2:
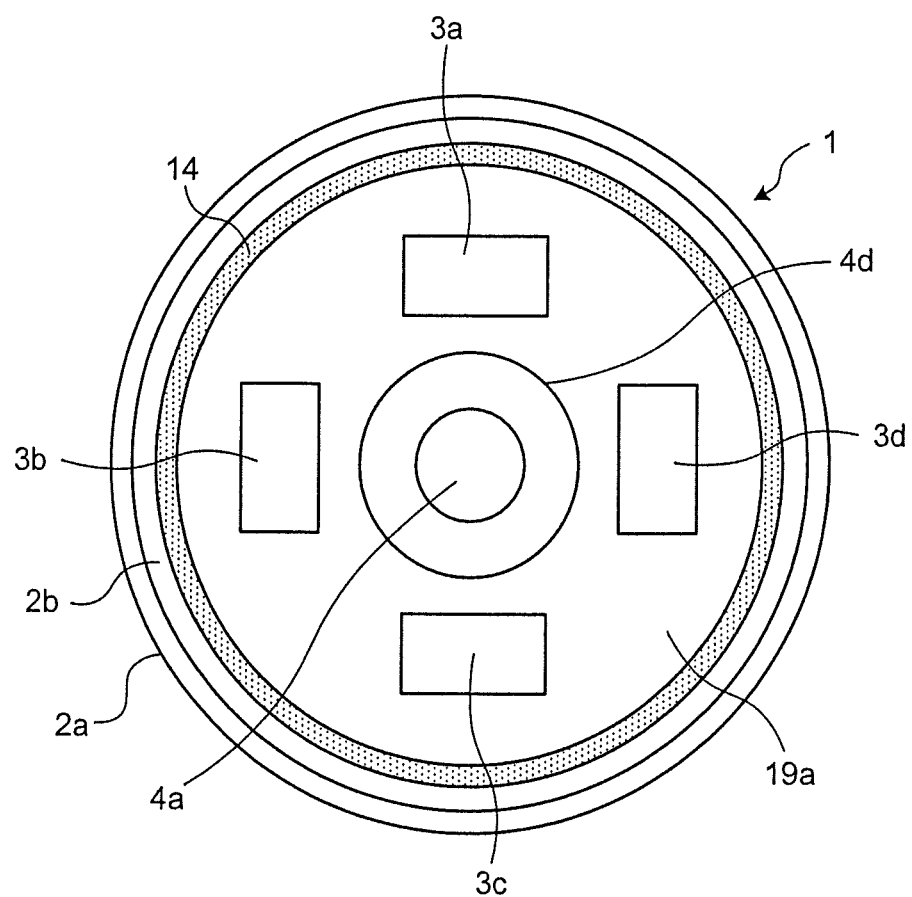
FIG. 2 is a schematic diagram illustrating an internal structure of the capsule endoscope as viewed across an optical dome from a direction F indicated in FIG. 1.
Figure 3:
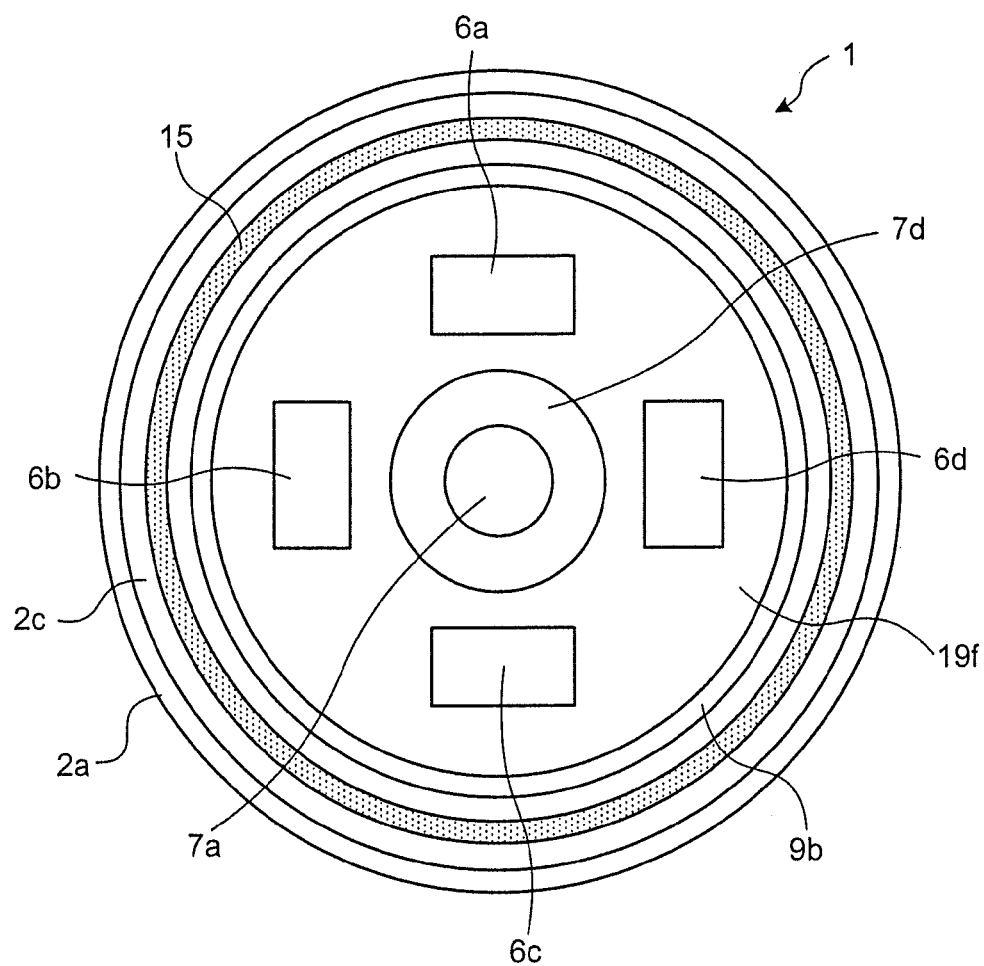
FIG. 3 is a schematic diagram illustrating an internal structure of the capsule endoscope as viewed across the optical dome from a direction B indicated in FIG. 1.

FIG. 1 is a schematic vertical sectional view of one configuration example of a capsule endoscope according to a first embodiment of the present invention. FIG. 2 is a schematic diagram illustrating an internal structure of the capsule endoscope viewed across an optical dome from a direction indicated by F in FIG. 1. FIG. 3 is a schematic diagram illustrating an internal structure of the capsule endoscope viewed across the optical dome from a direction indicated by B in FIG. 1.

As shown in FIG. 1, a capsule endoscope 1 according to the first embodiment of the present invention is a double-eyed-type capsule endoscope which picks up an intra-body image in a direction of F (forward direction) and an intra-body image in a direction of B (backward direction). The capsule endoscope 1 includes a capsule-like casing 2 which is formed in such a size that the capsule endoscope 1 can be introduced into the inside of the internal organ of the subject. Inside the casing 2, an imaging function for picking up an intra-body image in the direction of F, an imaging function for picking up an intra-body image in the direction of B, and a radio communication function for radio transmitting the intra-body image picked up by these imaging functions to an outside are provided.

More specifically, as shown in FIGS. 1 to 3, the capsule endoscope 1 includes in the casing 2, an illuminating substrate 19a on which plural light emitting elements 3a to 3d that illuminate the inside of the subject in the direction of F are mounted, an optical unit 4 which forms an image of the inside of the subject illuminated by the light emitting elements 3a to 3d, and an imaging substrate 19b on which a solid-state imaging element 5 that picks up an image of the inside of the subject formed by the optical unit 4 (in other words, an intra-body image in the direction of F) is mounted. Further, the capsule endoscope 1 includes, inside the casing 2, an illuminating substrate 19f on which plural light emitting elements 6a to 6d that illuminate the inside of the subject in the direction of B are mounted, an optical unit 7 which forms an image of the inside of the subject illuminated by the light emitting elements 6a to 6d, and an imaging substrate 19e on which a solid-state imaging element 8 that picks up an image of the inside of the subject formed by the optical unit 7 (in other words, an intra-body image in the direction of B) is mounted. Still further, the capsule endoscope 1 includes, inside the casing 2, a radio substrate 19d on which a radio unit 9a that radio transmits each of the intra-body images picked up by the solid-state imaging elements 5 and 8 to the outside via an antenna 9b is mounted, and a control substrate 19c on which a control unit 10 that controls the imaging function and the radio communication function is mounted.

Further, the capsule endoscope 1 includes, inside the casing 2, a power supply system for supplying power to the plural light emitting elements 3a to 3d, and 6a to 6d, the solid-state imaging elements 5 and 8, the radio unit 9a, and the control unit 10, more specifically, various circuit components such as a magnetic switch 11a, batteries 12a and 12b, power supply substrates 18a and 18b, and contact springs 13a and 13b that connect the batteries 12a and 12b with the power supply substrates 18a and 18b in a conductible manner. Further, the capsule endoscope 1 includes, in the casing 2, a positioning unit 14 that determines a relative position of each of the light emitting elements 3a to 3d and the optical unit 4 relative to an optical dome 2b arranged at a front end of the casing 2, a positioning unit 15 that determines a relative position of each of the light emitting elements 6a to 6d and the optical unit 7 relative to an optical dome 2c arranged at a rear end of the casing 2, a load receiving unit 16 that receives an elastic force of the contact spring 13a to secure the positioning unit 14 relative to the optical dome 2b, and a load receiving unit 17 that receives an elastic force of the contact spring 13b to secure the positioning unit 15 relative to the optical dome 2c.

The casing 2 is a capsule-like casing of such a size that the casing 2 can be easily introduced into the internal organ of the subject. The casing 2 is configured with a cylindrical trunk member 2a having a cylindrical structure and the optical domes 2b and 2c attached respectively to two open ends of the trunk member 2a. An outer diameter dimension of the cylindrical trunk member 2a is larger than that of each of the optical domes 2b and 2c. The cylindrical trunk member 2a is configured so that the optical domes 2b and 2c can be fitted to an inner circumferential surface near the open ends. On the inner circumferential surface near each of the open ends of the cylindrical trunk member 2a, a step is formed so as to contact with an end surface of a corresponding one of the optical domes 2b and 2c when the optical domes 2b and 2c are fitted thereto. When the end surfaces of the optical domes 2b and 2c are brought into contact with the steps of the cylindrical trunk member 2a, respectively, a relative position of each of the optical domes 2b and 2c relative to the cylindrical trunk member 2a is determined.

The optical domes 2b and 2c are optically transparent dome members formed in substantially uniform thickness. On an outer circumferential surface of each of the optical domes 2b and 2c near the open end, a concave portion is formed so as to engage with a convex portion formed on the inner circumferential surface of the cylindrical trunk member 2a near the open end. The optical dome 2b is fitted to the inner circumferential surface of the cylindrical trunk member 2a near the open end at the front side (a side indicated by F in FIG. 1), whereby the convex portion on the inner circumferential surface engages with the concave portion of the optical dome 2b and the optical dome 2b is secured at the front-side open end of the cylindrical trunk member 2a. Here, the end surface of the optical dome 2b is in contact with the step on the inner circumferential surface of the cylindrical trunk member 2a mentioned above. The optical dome 2b forms a part of the capsule-like casing 2 (more specifically, the optical dome 2b forms a front end portion of the casing 2). On the other hand, the optical dome 2c is fitted to the inner circumferential surface of the cylindrical trunk member 2a near the open end at the rear side (a side indicated by B in FIG. 1), whereby the convex portion on the inner circumferential surface engages with the concave portion of the optical dome 2c and the optical dome 2c is secured at the rear-side open end of the cylindrical trunk member 2a. Here, the end surface of the optical dome 2c is in contact with the step on the inner circumferential surface of the cylindrical trunk member 2a mentioned above. The optical dome 2c forms a part of the capsule-like casing 2 (in particular, a rear end portion). The casing 2 thus formed with the cylindrical trunk member 2a and the optical domes 2b and 2c houses, as shown in FIG. 1, each component of the capsule endoscope 1 in a watertight manner.

The light emitting elements 3a to 3d work as illuminating units that illuminate the inside of the subject in the direction F. Specifically, the light emitting elements 3a to 3d are light emitting elements such as LED and are mounted on the illuminating substrate 19a which is a flexible substrate formed in a substantially disk-like shape. Here, the light emitting elements 3a to 3d are mounted on the illuminating substrate 19a in such a manner that the light emitting elements 3a to 3d surround a lens frame 4d (mentioned later) of the optical unit 4 penetrating an opening of the illuminating substrate 19a as shown in FIGS. 1 and 2. The light emitting elements 3a to 3d emit predetermined illuminating light (such as white light) and illuminate the inside of the subject in the direction of F through the front-end side optical dome 2b.

The number of light emitting elements mounted on the illuminating substrate 19a is not specifically limited to four. As far as the light emitting element can emit the illuminating light of sufficient intensity for illuminating the inside of the subject in the direction of F, a single light emitting element or more may be enough. Further, as exemplified by the light emitting elements 3a to 3d, when plural light emitting elements are mounted on the illuminating substrate 19a, the plural light emitting elements are preferably mounted at rotationally-symmetric positions around a light axis of the optical unit 4 inserted in the opening of the illuminating substrate 19a.

The optical unit 4 collects the light reflected by the inside of the subject located in the direction of F and illuminated by the light emitting elements 3a to 3d, and forms an image of the inside of the subject in the direction of F. The optical unit 4 includes, for example, lenses 4a and 4b formed of glass, injection-molded plastic, and the like, a stop 4c arranged between the lenses 4a and 4b, and the lens frame 4d holding the lenses 4a and 4b and the stop 4c.

The lenses 4a and 4b collect the light reflected by the inside of the subject located in the direction of F and illuminated by the light emitting elements 3a to 3d, and form an image of the inside of the subject in the direction of F on a light acceptance surface of the solid-state imaging element 5. The stop 4c focuses (adjusts) brightness of the reflected light collected by the lenses 4a and 4b to a suitable level. The lens frame 4d has a cylindrical structure with two open ends, and holds the lenses 4a and 4b and the stop 4c in the cylindrical structure. The lens frame 4d is fitted into a through hole of a plate portion 14a (described later) of the positioning unit 14 and secured in such a state that the lens frame 4d penetrates through the opening formed in the illuminating substrate 19a. Thus, an upper end portion (an open end portion at the side of the lens 4a) and a trunk portion of the lens frame 4d protrude towards the illuminating substrate 19a side, and a lower end portion abuts a portion of the plate portion 14a around the through hole. The lens frame 4d thus secured at the plate portion 14a of the positioning unit 14 holds the lenses 4a and 4b at predetermined positions (i.e., suitable relative positions with respect to the optical dome 2b) determined by the positioning unit 14. Light axes of the lenses 4a and 4b can be made to coincide with a central axis CL of the casing 2 in the longitudinal direction.

Here, the lens 4b held by the lens frame 4d has a leg as shown in FIG. 1. With the leg pushed to an acceptance-side surface of the solid-state imaging element 5, a positional relation between the lens 4b and the solid-state imaging element 5 in a light-axis direction is determined. When the leg of the lens 4b is in contact with the acceptance-side surface of the solid-state imaging element 5, clearance is formed between the lower end portion of the lens frame 4d and the imaging substrate 19b. The clearance is filled up with a predetermined bonding agent, which bonds the lower end portion of the lens frame 4d and the imaging substrate 19b. Further, the bonding agent and the lens frame 4d serve to prevent unnecessary light from coming into the lenses 4a and 4b and the light acceptance surface of the solid-state imaging element 5.

The solid-state imaging element 5 is a solid-state imaging sensor having a light acceptance surface such as a CCD and CMOS (complementary metal-oxide semiconductor). The solid-state imaging element 5 works as an imaging unit that picks up an image of the inside of the subject in the direction of F illuminated by the light emitting elements 3a to 3d mentioned earlier. Specifically, the solid-state imaging element 5 is mounted (for example, in a manner of flip chip) on the imaging substrate 19*b* which is a flexible substrate formed in a substantially disk-like shape so that the light acceptance surface thereof faces against the lens 4*b* through the opening of the imaging substrate 19*b*. Here, the acceptance-side surface of the solid-state imaging element 5 is in contact with the leg of the lens 4*b*. With the imaging substrate 19*b* bonded to the lower end portion of the lens frame 4*d*, the contact state between the acceptance-side surface of the solid-state imaging element 5 and the leg of the lens 4*b* is maintained, and thus the solid-state imaging element 5 is fixedly arranged relative to the optical unit 4. The solid-state imaging element 5 receives light reflected from the inside of the subject and collected by the lenses 4*a* and 4*b* mentioned above through the acceptance surface, and picks up an image of the inside of the subject as formed by the lenses 4*a* and 4*b* on the acceptance surface (in other words, the intra-body image in the direction F).

The light emitting elements 6*a* to 6*d* work as illuminating units that illuminate the inside of the subject located in the direction of B. Specifically, the light emitting elements 6*a* to 6*d* are light emitting elements such as an LED, and are mounted on the illuminating substrate 19*f* which is a flexible substrate formed in a substantially disk-like shape. Here, the light emitting elements 6*a* to 6*d* are mounted on the illuminating substrate 19*f* in such a manner that the light emitting elements 6*a* to 6*d* surround a lens frame 7*d* (mentioned later) of the optical unit 7 which penetrates through the opening of the illuminating substrate 19*f* as shown in FIGS. 1 and 3. The light emitting elements 6*a* to 6*d* emit predetermined illuminating light (such as white light) to illuminate the inside of the subject in the direction of B through the rear-end side optical dome 2*c*.

The number of light emitting elements mounted on the illuminating substrate 19*f* is not particularly limited to four. As far as the light emitting element can emit the illuminating light of sufficient intensity for illuminating the inside of the subject in the direction of B, a single light emitting element or more may be enough. Further, as exemplified by the light emitting elements 6*a* to 6*d* mentioned above, when plural light emitting elements are mounted on the illuminating substrate 19*f*, the plural light emitting elements are preferably mounted at rotationally-symmetric positions around a light axis of the optical unit 7 inserted in the opening of the illuminating substrate 19*f*.

The optical unit 7 collects the light reflected from the inside of the subject in the direction of B illuminated by the light emitting elements 6*a* to 6*d* mentioned above, and forms an image of the inside of the subject in the direction of B. The optical unit 7 includes, for example, lenses 7*a* and 7*b* formed of glass, injection-molded plastic, and the like, a stop 7*c* arranged between the lenses 7*a* and 7*b*, and the lens frame 7*d* holding the lenses 7*a* and 7*b* and the stop 7*c*.

The lenses 7*a* and 7*b* collect the light reflected by the inside of the subject located in the direction of B and illuminated by the light emitting elements 6*a* to 6*d*, and form an image of the inside of the subject in the direction of B on a light acceptance surface of the solid-state imaging element 8. The stop 7*c* focuses (adjusts) brightness of the reflected light collected by the lenses 7*a* and 7*b* to a suitable level. The lens frame 7*d* has a cylindrical structure with two open ends, and holds the lenses 7*a* and 7*b* and the stop 7*c* in the cylindrical structure. The lens frame 7*d* is fitted into a through hole of a plate portion 15*a* (described later) of the positioning unit 15 in a state penetrating through the opening formed in the illuminating substrate 19*f*. Thus, an upper end portion (an open end portion at the side of the lens 7*a*) and a trunk portion of the lens frame 7*d* protrude towards the illuminating substrate 19*f* side, and a lower end portion abuts a portion of the plate portion 15*a* around the through hole. The lens frame 7*d* thus secured at the plate portion 15*a* of the positioning unit 15 holds the lenses 7*a* and 7*b* at predetermined positions (i.e., suitable relative positions with respect to the optical dome 2*c*) determined by the positioning unit 15. Light axes of the lenses 7*a* and 7*b* can be made to coincide with the central axis CL of the casing 2 in the longitudinal direction.

Here, the lens 7*b* held by the lens frame 7*d* has a leg (see FIG. 1) similarly to the lens 4*b* of the optical unit 4 mentioned earlier. With the leg pushed to an acceptance-side surface of the solid-state imaging element 8, a positional relation between the lens 7*b* and the solid-state imaging element 8 in a light-axis direction is determined. When the leg of the lens 7*b* is in contact with the acceptance-side surface of the solid-state imaging element 8, clearance is formed between the lower end portion of the lens frame 7*d* and the imaging substrate 19*e*. The clearance is filled up with a predetermined bonding agent, which bonds the lower end portion of the lens frame 7*d* and the imaging substrate 19*e*. Further, the bonding agent and the lens frame 7*d* serve to prevent unnecessary light from coming into the lenses 7*a* and 7*b*, and the light acceptance surface of the solid-state imaging element 8.

The solid-state imaging element 8 is a solid-state imaging sensor having a light acceptance surface such as a CCD and CMOS. The solid-state imaging element 8 works as an imaging unit that picks up an image of the inside of the subject in the direction of B illuminated by the light emitting elements 6*a* to 6*d* mentioned earlier. Specifically, the solid-state imaging element 8 is mounted (for example, in a manner of flip chip) on the imaging substrate 19*e* which is a flexible substrate formed in a substantially disk-like shape so that the light acceptance surface thereof faces against the lens 7*b* through the opening of the imaging substrate 19*e*. Here, the acceptance-side surface of the solid-state imaging element 8 is in contact with the leg of the lens 7*b*. With the imaging substrate 19*e* bonded to the lower end portion of the lens frame 7*d*, the contact state between the acceptance-side surface of the solid-state imaging element 8 and the leg of the lens 7*b* is maintained, and thus the solid-state imaging element 8 is fixedly arranged relative to the optical unit 7. The solid-state imaging element 8 receives light reflected from the inside of the subject and collected by the lenses 7*a* and 7*b* mentioned above through the light acceptance surface, and picks up an image of the inside of the subject as formed by the lenses 7*a* and 7*b* on the light acceptance surface (in other words, the intra-body image in the direction B).

The radio unit 9*a* and the antenna 9*b* work to realize a radio communication function for radio transmitting each of the intra-body images in the direction of F or the direction of B as picked up by the solid-state imaging elements 5 and 8 to the outside. Specifically, the radio unit 9*a* is mounted on the radio substrate 19*d* which is a flexible substrate formed in a substantially disk-like shape, and is arranged inside the casing 2 in such a manner that the radio unit 9*a* faces against the imaging substrate 19*e* on which the solid-state imaging element 8 is mounted. The antenna 9*b* is fixedly arranged on the illuminating substrate 19*f* which is secured on the surface of the plate portion 15*a* of the positioning unit 15 as shown in FIGS. 1 and 3, and is connected to the radio unit 9*a* via the radio substrate 19*d*, the illuminating substrate 19*f*, and the like. The antenna 9*b* is fixedly arranged on an outer periphery of the illuminating substrate 19*f* facing the optical dome 2c at the rear end side, at an outer position in comparison with the light emitting elements 6a to 6d mentioned earlier.

Every time the radio unit 9a receives an image signal including an intra-body image in the direction of F as picked up by the solid-state imaging element 5, the radio unit 9a generates a radio signal including an intra-body image in the direction of F by performing modulation process and the like on the received image signal, and transmits the generated radio signal to the outside via the antenna 9b. On the other hand, every time the radio unit 9a receives an image signal including an intra-body image in the direction of B as picked up by the solid-state imaging element 8, the radio unit 9a generates a radio signal including an intra-body image in the direction of B by performing modulation process and the like on the received image signal, and transmits the generated radio signal to the outside via the antenna 9b. The radio unit 9a generates the radio signal including an intra-body image in the direction of F and the radio signal including an intra-body image in the direction of B alternately based on the control by the control unit 10, and transmits generated radio signals alternately.

The control unit 10 is a processor such as a DSP (digital signal processor) and is arranged substantially at the center in the casing 2 in a state mounted on the control substrate 19c which is a rigid substrate formed substantially in a disk-like shape. The control unit 10 is electrically connected to the illuminating substrates 19a, 19f, the imaging substrates 19b and 19e, and the radio substrate 19d via the control substrate 19c and the flexible substrate. The control unit 10 controls the light-emitting elements 3a to 3d mounted on the illuminating substrate 19a, the light emitting elements 6a to 6d mounted on the illuminating substrate 19f, the solid-state imaging elements 5 and 8 mounted respectively on the imaging substrates 19b and 19e, and the radio unit 9a mounted on the radio substrate 19d. Specifically, the control unit 10 controls operation timing of the light emitting elements 3a to 3d and the solid-state imaging element 5 so that the solid-state imaging element 5 picks up an intra-body image in the direction of F at a predetermined time interval in synchronization with a light emitting operation of the light emitting elements 3a to 3d. Similarly, the control unit 10 controls operation timing of the light emitting elements 6a to 6d and the solid-state imaging element 8 so that the solid-state imaging element 8 picks up an intra-body image in the direction of B at a predetermined time interval in synchronization with a light emitting operation of the light emitting elements 6a to 6d. Further, the control unit 10 controls the radio unit 9a so as to radio transmit the intra-body image in the direction of F and the intra-body image in the direction of B alternately. The control unit 10 has various parameters related with imaging processing such as white balance, and has an image processing function for sequentially generating an image signal including an intra-body image in the direction of F as picked up by the solid-state imaging element 5 and an image signal including an intra-body image in the direction of B as picked up by the solid-state imaging element 8.

Figure 4:
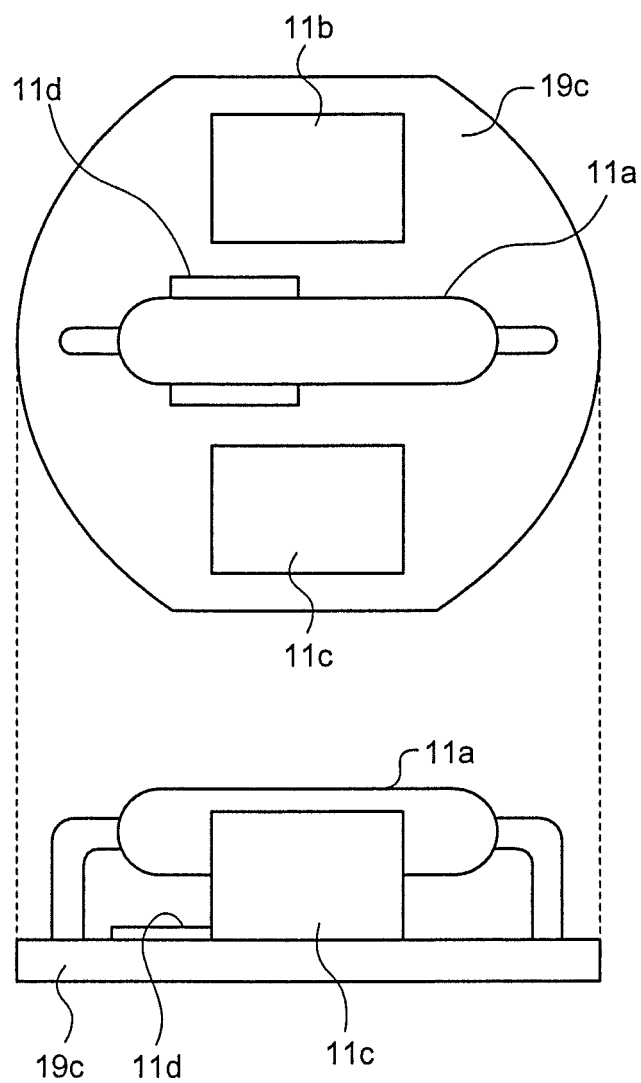
FIG. 4 is a schematic diagram illustrating a state where circuit components of a power supply system are mounted on a control substrate.

On the other hand, on the control substrate 19c, various circuit components such as circuit components of the power supply system, specifically circuit components such as the magnetic switch 11a are mounted on a substrate surface opposite from the substrate surface where the control unit 10 is mounted. FIG. 4 is a schematic diagram illustrating a state where the circuit components of the power supply system are mounted on the control substrate 19c. As shown in FIGS. 1 and 4, on one substrate surface of the control substrate 19c, the circuit components of the power supply system such as the magnetic switch 11a, capacitors 11b and 11c, and a power supply IC 11d are mounted. Here, the capacitors 11b and 11c, and the power supply IC 11d are surface mounted on the control substrate 19c, while the magnetic switch 11a is mounted on the control substrate 19c in such a manner that lead lines extending from two sides of the magnetic switch 11a extend across the power supply IC 11d. The magnetic switch 11a switches the state between on and off by applying an external magnetic field in a predetermined direction. In the on state, the magnetic switch 11a starts supplying power from the batteries 12a and 12b to the light emitting elements 3a to 3d, 6a to 6d, the solid-state imaging elements 5 and 8, the radio unit 9a, and the control unit 10, whereas in the off state, the magnetic switch 11a stops the power supply from the batteries 12a and 12b. On the other hand, the power supply IC 11d has a power supply control function for controlling the power supply to each component via the magnetic switch 11a.

The batteries 12a and 12b generate electric power to operate the light emitting elements 3a to 3d, 6a to 6d, the solid-state imaging elements 5 and 8, the radio unit 9a, and the control unit 10. Specifically, the batteries 12a and 12b are button-type batteries such as silver oxide batteries, and are held between the load receiving units 16 and 17 by an end portion of the positioning unit 14 and an end portion of the load receiving unit 17 as shown in FIG. 1. Here, on each surface of the load receiving units 16 and 17, facing the batteries 12a and 12b, respectively, power supply substrates 18a and 18b are arranged respectively so as to be electrically connected to the control substrate 19c via the flexible substrate or the like. Further, the current carrying contact springs 13a and 13b are arranged on the power supply substrates 18a and 18b, respectively. The batteries 12a and 12b arranged between the load receiving units 16 and 17 are held by the end portion of the positioning unit 14 and the end portion of the load receiving unit 17 with the contact springs 13a and 13b in a compressed state, and are electrically connected to the circuit components of the power supply system (i.e., the magnetic switch 11a, the capacitors 11b and 11c, and the power supply IC 11d) on the control substrate 19c via the contact springs 13a and 13b in the compressed state and the power supply substrates 18a and 18b. The number of batteries arranged in the casing 2 is not specifically limited to two as far as the batteries can supply sufficient amount of power.

To the positioning unit 14, the illuminating substrate 19a on which the light emitting elements 3a to 3d are mounted and the optical unit 4 are fixedly arranged, and the positioning unit 14 is fitted and secured on an inner circumferential surface of the optical dome 2b at the front end side. The positioning unit 14 thus fitted and secured on the inner circumferential surface of the optical dome 2b fixes the positional relations among the optical dome 2b, the light emitting elements 3a to 3d, and the optical unit 4, so as to determine a suitable relative position of each of the light emitting elements 3a to 3d and the optical unit 4 relative to the optical dome 2b. The positioning unit 14 is configured with the plate portion 14a fitted to the inner circumferential surface of the optical dome 2b and a protruding portion 14b serving for securing the plate portion 14a at a predetermined position on the inner circumferential surface of the optical dome 2b.

The plate portion 14a is a plate-like member having a substantially disk-like shape with an outer diameter dimension corresponding to the inner diameter dimension of the optical dome 2b, and has an outer circumferential surface fitting to the inner circumferential surface of the optical dome 2b. Further, on the plate portion 14a, the illuminating substrate 19a mentioned earlier and the optical unit 4 are fixedly arranged. Specifically, the illuminating substrate 19a is fixedly arranged on a surface of the plate portion 14a which faces the optical dome 2b when the plate portion 14a is fitted to the inner circumferential surface of the optical dome 2b. Further, the plate portion 14a has a through hole communicating with the opening formed in the illuminating substrate 19a substantially at the center thereof, and the lens frame 4d of the optical unit 4 is inserted and fixed (for example, securely fitted) in the through hole. The lens frame 4d inserted and secured in the through hole of the plate portion 14a makes its upper end portion and trunk portion protruding at the side of the illuminating substrate 19a while penetrating the opening of the illuminating substrate 19a as described above. The plate portion 14a fixes the positional relations between the lens frame 4d and the light emitting elements 3a to 3d so that each of the upper end portions of the light emitting elements 3a to 3d is arranged at a level lower than the upper end portion of the lens frame 4d.

The protruding portion 14b protrudes from the plate portion 14a mentioned earlier and engages with the open end of the optical dome 2b so as to fix the plate portion 14a on the inner circumferential surface of the optical dome 2b. Specifically, the protruding portion 14b is formed integrally with the plate portion 14a and protrudes from a back surface of the plate portion 14a opposite to the side where the illuminating substrate 19a is fixedly arranged. The protruding portion 14b has a cylindrical structure having an outer diameter dimension corresponding to the inner diameter dimension of the optical dome 2b (in other words, an outer diameter dimension equivalent to that of the plate portion 14a), and has a flange portion engaging with the open end of the optical dome 2b in an open end portion of the cylindrical structure. The protruding portion 14b having the above-described structure is fitted to the inner circumferential surface of the optical dome 2b together with the plate portion 14a mentioned earlier and its flange portion engages with the open end of the optical dome 2b. Thus, the protruding portion 14b secures the plate portion 14a at a predetermined position on the inner circumferential surface of the optical dome 2b.

To the positioning unit 15, the illuminating substrate 19f on which the light emitting elements 6a to 6d are mounted and the optical unit 7 are fixedly arranged, and the positioning unit 15 is fitted and secured on the inner circumferential surface of the optical dome 2c in the rear end side. The positioning unit 15 fitted and secured on the inner circumferential surface of the optical dome 2c fixes the positional relation among the optical dome 2c, the light emitting elements 6a to 6d, and the optical unit 7, so as to determine a suitable relative position of each of the light emitting elements 6a to 6d and the optical unit 7 relative to the optical dome 2c. The positioning unit 15 is configured with the plate portion 15a fitted to the inner circumferential surface of the optical dome 2c and a protruding portion 15b which serves to fix the plate portion 15a at a predetermined position on the inner circumferential surface of the optical dome 2c.

The plate portion 15a is a plate-like member having a substantially disk-like shape having an outer diameter dimension corresponding to the inner diameter dimension of the optical dome 2c, and has an outer circumferential surface fitted to the inner circumferential surface of the optical dome 2c. Further, the illuminating substrate 19f mentioned earlier and the optical unit 7 are fixedly arranged on the plate portion 15a. Specifically, the illuminating substrate 19f is fixedly arranged on a surface of the plate portion 15a facing the optical dome 2c when the plate portion 15a is fitted to the inner circumferential surface of the optical dome 2c. Further, the plate portion 15a has a through hole communicating with the opening formed in the illuminating substrate 19f in substantially the center thereof, and the lens frame 7d of the optical unit 7 is inserted and secured (for example, fitted and secured) in the through hole. The lens frame 7d inserted and secured in the through hole of the plate portion 15a makes its upper end portion and trunk portion protrude at the side of the illuminating substrate 19f while penetrating the opening of the illuminating substrate 19f. The plate portion 15a fixes the positional relation between the lens frame 7d and each of the light emitting elements 6a to 6d so that each of the upper end portions of the light emitting elements 6a to 6d is arranged at a level lower than the upper end portion of the lens frame 7d.

The protruding portion 15b protrudes from the plate portion 15a mentioned earlier and engages with the open end of the optical dome 2c to secure the plate portion 15a on the inner circumferential surface of the optical dome 2c. Specifically, the protruding portion 15b is formed integrally with the plate portion 15a so as to protrude from the back surface of the plate portion 15a opposite to the side where the illuminating substrate 19f is fixedly arranged. The protruding portion 15b has a cylindrical structure having an outer diameter dimension corresponding to the inner diameter dimension of the optical dome 2c (i.e., outer diameter dimension equivalent to that of the plate portion 15a), and has a flange portion engaging with the open end of the optical dome 2c at the open end portion of the cylindrical structure. The protruding portion 15b having the above-described structure is fitted to the inner circumferential surface of the optical dome 2c together with the plate portion 15a so as to make the flange portion engage with the open end of the optical dome 2c. Thus, the protruding portion 15b fixes the plate portion 15a at a predetermined position on the inner circumferential surface of the optical dome 2c.

The load receiving unit 16 receives an elastic force of the contact spring 13a mentioned earlier to press and secure the positioning unit 14 at the open end of the optical dome 2b by the elastic force. Specifically, the load receiving unit 16 is a plate-like member of a substantially disk-like shape making its outer periphery engaging with a step formed around the inner peripheral side of the protruding portion 14b of the positioning unit 14. As mentioned earlier, the load receiving unit 16 has the power supply substrate 18a and the contact spring 13a on the surface facing the battery 12a. The load receiving unit 16 receives the elastic force of the contact spring 13a generated along the compression of the contact spring 13a mentioned earlier so as to press and secure the flange portion of the protruding portion 14b to the open end of the optical dome 2b by the elastic force of the contact spring 13a. Here, the load receiving unit 16 presses and secures the protruding portion 14b against the open end of the optical dome 2b so that the plate portion 14a which is integral with the protruding portion 14b is fitted and secured at a predetermined position on the inner circumferential surface of the optical dome 2b.

The load receiving unit 16 has, as shown in FIG. 1, a through hole for preventing a contact with the circuit components such as a capacitor mounted on the imaging substrate 19b. Further, when the load receiving unit 16 engages with the step on the inner circumferential side of the protruding portion 14b, the load receiving unit 16 and the positioning unit 14 form a sufficient space for arrangement of the solid-state imaging element 5 in contact with the leg of the lens 4*b*, and the imaging substrate 19*b* in a state secured against the lower end portion of the lens frame 4*d* as shown in FIG. 1.

The load receiving unit 17 receives the elastic force of the contact spring 13*b* mentioned earlier, and presses and secures the positioning unit 15 against the open end of the optical dome 2*c* by the elastic force. Specifically, the load receiving unit 17 has a cylindrical structure having an outer diameter dimension slightly smaller than the inner diameter dimension of the cylindrical trunk member 2*a* of the casing 2, and has a plate-like portion facing the battery 12*b* at one open end side of the cylindrical structure.

The cylindrical structure of the load receiving unit 17 works as a spacer forming a predetermined space inside the casing 2, and makes another open end thereof engaging with the open end portion (flange portion) of the protruding portion 15*b* of the positioning unit 15. Here, the cylindrical structure of the load receiving unit 17 and the positioning unit 15 form a sufficient space for arrangement of the control substrate 19*c* on which the circuit components such as the control unit 10 and the magnetic switch 11*a* are mounted, the radio substrate 19*d* on which the radio unit 9*a* is mounted, the solid-state imaging element 8 in contact with the leg of the lens 7*b*, and the imaging substrate 19*e* in a state secured to the lower end portion of the lens frame 7*d* as shown in FIG. 1.

The plate-like portion of the load receiving unit 17 is integrally formed at one open end side of the cylindrical structure of the load receiving unit 17, and has the power supply substrate 18*b* and the contact spring 13*b* on the surface facing the battery 12*b* as shown in FIG. 1. Further, the plate-like portion of the load receiving unit 17 has a through hole for preventing a contact with the circuit components such as a capacitor mounted on the control substrate 19*c* arranged in the space formed by the cylindrical structure of the load receiving unit 17 mentioned above. The plate-like portion of the load receiving unit 17 receives an elastic force of the contact spring 13*b* generated along with the compression of the contact spring 13*b* mentioned earlier, and presses the cylindrical structure of the load receiving unit 17 against the open end portion of the protruding portion 15*b* of the positioning unit 15 by the elastic force of the contact spring 13*b*.

The load receiving unit 17 having the cylindrical structure and the plate-like portion as described above presses and secures the flange portion of the protruding portion 15*b* against the open end portion of the optical dome 2*c* by the elastic force of the contact spring 13*b*. Here, the load receiving unit 17 presses and secures the protruding portion 15*b* against the open end portion of the optical dome 2*c* so that the plate portion 15*a* which is integral with the protruding portion 15*b* is fitted and secured at a predetermined position on the inner circumferential surface of the optical dome 2*c*.

Figure 5:
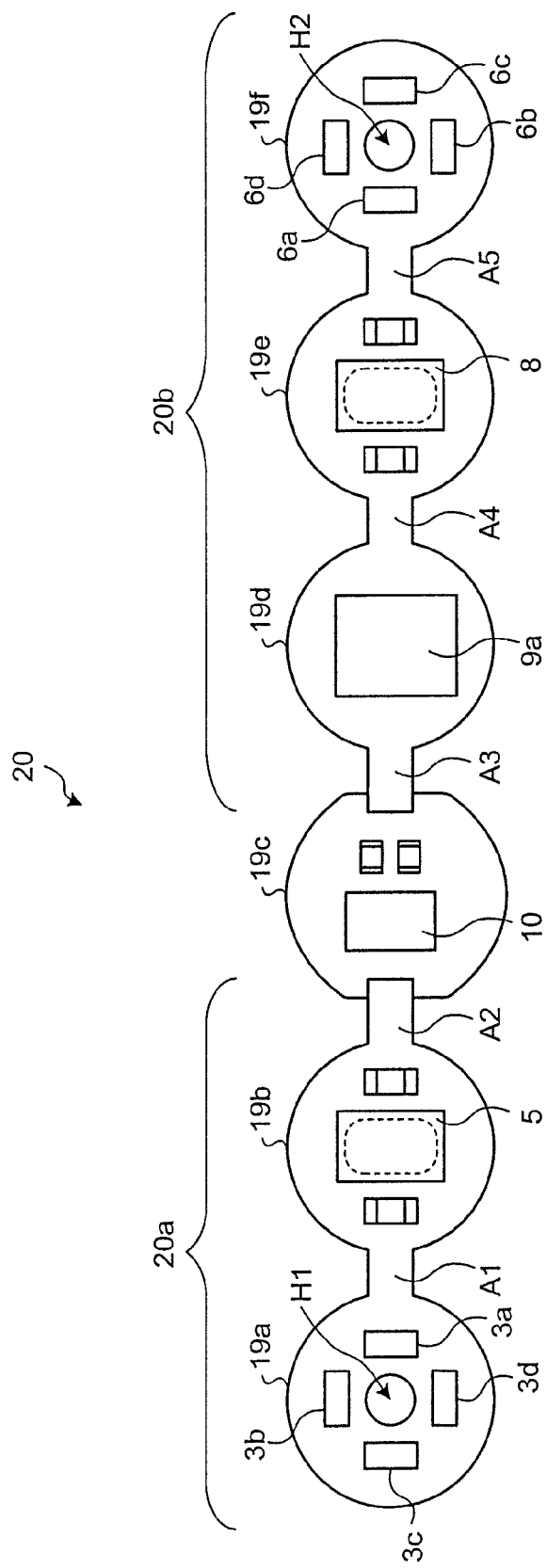
FIG. 5 is a schematic diagram illustrating an extended state of a string of circuit substrates which is arranged in a folded state in a casing of the capsule endoscope.

A string of circuit substrates (specifically, the illuminating substrates 19*a*, 19*f*, the imaging substrates 19*b*, 19*e*, the control substrate 19*c*, and the radio substrate 19*d*) arranged inside the casing 2 of the capsule endoscope 1 will be described. FIG. 5 is a schematic diagram illustrating in an extended state the string of circuit substrates which is arranged inside the casing 2 of the capsule endoscope 1 in a folded state. In the following, each substrate surface of the flexible substrate or the rigid substrate shown in FIG. 5 is defined as a front-side substrate surface (front substrate surface) and the substrate surface opposite to the front substrate surface shown is defined as a back-side substrate surface (back substrate surface).

As shown in FIG. 5, a string of circuit substrates 20 arranged inside the casing 2 of the capsule endoscope 1 is realized through electrical connection of a string of flexible substrates 20*a* configured with the illuminating substrate 19*a* and the imaging substrate 19*b* coupled with each other and a string of flexible substrates 20*b* configured with the control substrate 19*c* which is a rigid substrate, the radio substrate 19*d*, the imaging substrate 19*e*, and the illuminating substrate 19*f* coupled with each other.

The illuminating substrate 19*a* is a substantially disk-like flexible substrate on which circuits are formed to realize an illuminating function for illuminating the subject in the direction of F of the capsule endoscope 1. On the front substrate surface of the illuminating substrate 19*a*, plural light emitting elements 3*a* to 3*d* mentioned earlier are mounted, and at the center of the substrate surface of the illuminating substrate 19*a* surrounded by the light emitting elements 3*a* to 3*d*, an opening H1 is formed so that the lens frame 4*d* of the optical unit 4 in which the leg of the lens 4*b* is in contact with the solid-state imaging element 5 can be inserted thereto. The illuminating substrate 19*a* is electrically connected to the imaging substrate 19*b* via an extending portion A1 which is a flexible substrate portion extending from an outer peripheral portion.

The imaging substrate 19*b* is a substantially disk-like flexible substrate on which circuits are formed to realize an imaging function of imaging an intra-body image in the direction of F. On the front substrate surface of the imaging substrate 19*b*, the solid-state imaging element 5 mentioned earlier is flip-chip mounted and further, circuit components such as a capacitor are mounted as necessary. In the imaging substrate 19*b*, an opening is formed as indicated by a dotted line in FIG. 5 so that the light reflected by the inside of the subject in the direction of F is incident on the light acceptance surface of the solid-state imaging element 5 thus flip-chip mounted. Here, though not specifically shown in FIG. 5, the lower end portion of the lens frame 4*d* of the optical unit 4 is secured on the back substrate surface of the imaging substrate 19*b* as shown in FIG. 1. In the optical unit 4, the leg of the lens 4*b* is in contact with the acceptance-side surface of the solid-state imaging element 5 via the opening of the imaging substrate 19*b*. To the imaging substrate 19*b*, the control substrate 19*c* is electrically connected via an extending portion A2 which is a flexible substrate portion extending from the outer peripheral portion thereof.

The control substrate 19*c* is a substantially disk-like rigid substrate on which necessary circuits such as the magnetic switch 11*a* are formed for the power supply system and the control unit 10. On the front substrate surface of the control substrate 19*c*, the control unit 10 mentioned earlier is mounted, and further, circuit components such as a capacitor are mounted as necessary. On the other hand, on the back substrate surface of the control substrate 19*c*, circuit components of the power supply system, i.e., the magnetic switch 11*a*, the capacitors 11*b* and 11*c*, and the power supply IC 11*d* are mounted as shown in FIG. 4. The control substrate 19*c* is electrically connected to the radio substrate 19*d* via an extending portion A3 which is a flexible substrate portion extending from the outer peripheral portion of the radio substrate 19*d*. Here, the control substrate 19*c* is electrically connected to the power supply substrates 18*a* and 18*b* mentioned earlier via a flexible substrate and the like (not shown) though not specifically shown in FIG. 5.

The radio substrate 19*d* is a substantially disk-like flexible substrate on which circuits are formed to realize a radio communication function for sequentially radio transmitting the intra-body image in the direction of F and the intra-body image in the direction of B to the outside. On the front substrate surface of the radio substrate 19d, the radio unit 9a mentioned earlier is mounted. Though not specifically shown in FIG. 5, the radio substrate 19d is electrically connected to the antenna 9b fixedly arranged on the outer peripheral portion of the illuminating substrate 19f as shown in FIGS. 1 and 3. The radio substrate 19d is electrically connected to the imaging substrate 19e via an extending portion A4 which is a flexible substrate portion extending from the outer peripheral portion.

The imaging substrate 19e is a substantially disk-like flexible substrate on which circuits are formed to realize an imaging function for picking up an intra-subject image in the direction of B. On the front substrate surface of the imaging substrate 19e, the solid-state imaging element 8 is flip-chip mounted, and further, circuit components such as a capacitor are mounted as necessary. In the imaging substrate 19e, an opening is formed as indicated by the dotted line of FIG. 5 so that the light reflected by the inside of the subject in the direction of B is incident on the light acceptance surface of the solid-state imaging element 8 thus flip-chip mounted. Here, though not specifically shown in FIG. 5, the lower end portion of the lens frame 7d of the optical unit 7 is secured on the back substrate surface of the imaging substrate 19e as shown in FIG. 1. In the optical unit 7, the leg of the lens 7b is in contact with the acceptance-side surface of the solid-state imaging element 8 via the opening of the imaging substrate 19e. The imaging substrate 19e is electrically connected to the illuminating substrate 19f via an extending portion A5 which is a flexible substrate portion extending from the outer peripheral portion.

The illuminating substrate 19f is a substantially disk-like flexible substrate on which circuits are formed to realize an illuminating function for illuminating the subject in the direction of B of the capsule endoscope 1. On the front substrate surface of the illuminating substrate 19f, plural light emitting elements 6a to 6d are mounted. At the center of the substrate surface of the illuminating substrate 19f surrounded by the light emitting elements 6a to 6d, an opening H2 is formed so that the lens frame 7d of the optical unit 7 in which the leg of the lens 7b is in contact with the solid-state imaging element 8 can be inserted thereto.

The string of flexible substrates 20a is an integral flexible substrate having the illuminating substrate 19a and the imaging substrate 19b mentioned earlier, and has a substrate structure in which the imaging substrate 19b having the extending portion A2 extending from the outer peripheral portion for the connection to the control substrate 19c is connected to the illuminating substrate 19a via the extending portion A1. On the other hand, the string of flexible substrates 20b is an integral flexible substrate including the radio substrate 19d, the imaging substrate 19e, and the illuminating substrate 19f, and has a substrate structure in which the radio substrate 19d having the extending portion A3 extending from the outer peripheral portion for the connection to the control substrate 19c is connected to the imaging substrate 19e via the extending portion A4, and a substrate structure in which the imaging substrate 19e and the illuminating substrate 19f are connected with each other via the extending portion A5. The string of circuit substrates 20 arranged inside the casing 2 of the capsule endoscope 1 is configured with the string of flexible substrates 20a and 20b connected to the control substrate 19c via the extending portions A2 and A3.

A method of manufacturing the capsule endoscope 1 according to the first embodiment of the present invention will be described. The capsule endoscope 1 is manufactured by: manufacturing the string of circuit substrates 20 shown in FIG. 5; manufacturing a functional unit by combining the string of circuit substrates 20 manufactured, the positioning units 14 and 15, the load receiving units 16 and 17, and the batteries 12a and 12b; and arranging the functional unit manufactured inside the casing 2.

More specifically, first, necessary components are mounted on the illuminating substrate 19a and the imaging substrate 19b of the string of flexible substrates 20a, necessary components are mounted on the control substrate 19c, and necessary components are mounted on the radio substrate 19d, the imaging substrate 19e, and the illuminating substrate 19f of the string of flexible substrates 20b. Here, in the string of flexible substrates 20a, plural light emitting elements 3a to 3d are mounted on the front substrate surface of the illuminating substrate 19a, circuit components such as the solid-state imaging element 5 and a capacitor are mounted on the front substrate surface of the imaging substrate 19b, and the optical unit 4 is mounted on the back substrate surface of the imaging substrate 19b in such a manner that the solid-state imaging element 5 is in contact with the leg of the lens 4b. Further, in the string of flexible substrate 20b, plural light emitting element 6a to 6d, and the antenna 9b are mounted on the front substrate surface of the illuminating substrate 19f, circuit components such as the solid-state imaging element 8 and the capacitor are mounted on the front substrate surface of the imaging substrate 19e, and the optical unit 7 is mounted on the back substrate surface of the imaging substrate 19e in such a manner that the solid-state imaging element 8 is in contact with the leg of the lens 7b. On the other hand, on the front substrate surface of the control substrate 19c, the circuit components such as the control unit 10 and the capacitor are mounted, and on the back substrate surface of the control substrate 19c, the circuit components of the power supply system such as the magnetic switch 11a are mounted. When the strings of flexible substrates 20a and 20b are connected with the control substrate 19c, the string of circuit substrates 20 is manufactured.

The lens frame 4d of the optical unit 4 is a separate member from the positioning unit 14 mentioned earlier. The lens frame 4d is mounted on the back substrate surface of the imaging substrate 19b before the lens frame 4d is fitted and secured in the through hole of the positioning unit 14 (more specifically, the plate portion 14a) as shown in FIG. 1. Thus, a necessary space for applying a bonding agent to a clearance between the imaging substrate 19b and the lower end portion of the lens frame 4d can be secured sufficiently, and the lens frame 4d can be easily secured to the imaging substrate 19b with the bonding agent. The same applies to the lens frame 7d mounted on the back substrate surface of the imaging substrate 19e.

Then, the functional unit of the capsule endoscope 1 is manufactured by combining the string of circuit substrates 20 manufactured as described above, the positioning units 14 and 15, the load receiving units 16 and 17, and the batteries 12a and 12b. The functional unit is a portion other than the casing 2 of the capsule endoscope 1 shown in FIG. 1 (in other words, a unit arranged inside the casing 2).

In the functional unit, the lens frame 4d of the optical unit 4 mounted on the imaging substrate 19b is fitted and secured in the through hole formed in the plate portion 14a of the positioning unit 14. On one surface of the plate portion 14a (a surface facing the optical dome 2b), a bonding agent or a double-sided adhesive tape is applied or pasted as a bonding member so that the illuminating substrate 19a is secured to the plate portion 14a by the bonding member in such a manner that the lens frame 4*d* penetrates through the opening H1. Then, the outer peripheral portion of the load receiving unit 16 is made to engage with the protruding portion 14*b* of the positioning unit 14 to which the illuminating substrate 19*a*, the imaging substrate 19*b*, and the like are attached. Here, the load receiving unit 16 is attached to the protruding portion 14*b* so as to arrange the power supply substrate 18*a* and the contact spring 13*a* on a surface opposite to a surface facing the solid-state imaging element 5 on the imaging substrate 19*b*.

On the other hand, the lens frame 7*d* of the optical unit 7 mounted on the imaging substrate 19*e* is fitted and secured in the through hole formed in the plate portion 15*a* of the positioning unit 15. On one surface of the plate portion 15*a* (a surface facing the optical dome 2*c*), a bonding agent or a double-sided adhesive tape is applied or pasted as a bonding member, and the illuminating substrate 19*f* is secured to the plate portion 15*a* by the bonding member in such a manner that the lens frame 7*d* penetrates through the opening H2. The end portion of the cylindrical structure of the load receiving unit 17 engages with the protruding portion 15*b* of the positioning unit 15 to which the illuminating substrate 19*f*, the imaging substrate 19*e*, and the like are attached. Here, the load receiving unit 17 is attached to the protruding portion 15*b* in such a manner that the control substrate 19*c* and the radio substrate 19*d* are arranged inside the space formed by the cylindrical structure, and that the power supply substrate 18*a* and the contact spring 13*a* of the load receiving unit 16 are arranged opposite to the power supply substrate 18*b* and the contact spring 13*b*.

Further, the batteries 12*a* and 12*b* are arranged between the load receiving units 16 and 17 which arrange the power supply substrate 18*a* and the contact spring 13*a* opposite to the power supply substrate 18*b* and the contact spring 13*b*. The batteries 12*a* and 12*b* are held by the protruding portion 14*b* of the positioning unit 14 and the end portion of the load receiving unit 17 in such a manner that the positive terminal of the battery 12*a* is in contact with the negative terminal of the battery 12*b*. The batteries 12*a* and 12*b* compress the contact springs 13*a* and 13*b*, and thus electrically connected to the power supply substrates 18*a* and 18*b* via the contact springs 13*a* and 13*b*, respectively.

In the manner as described above, the functional unit of the capsule endoscope 1 is manufactured. The string of circuit substrates 20 embedded in the functional unit is folded in a predetermined manner. Here, as shown in FIG. 1, the back substrate surface of the illuminating substrate 19*a* and the back substrate surface of the imaging substrate 19*b* face with each other across the plate portion 14*a* of the positioning unit 14, and the front substrate surface of the imaging substrate 19*b* and the front substrate surface of the control substrate 19*c* face with each other across the load receiving units 16 and 17, the batteries 12*a* and 12*b*, and the like. Further, the back substrate surface of the control substrate 19*c* faces against the back substrate surface of the radio substrate 19*d*, the front substrate surface of the radio substrate 19*d* faces against the front substrate surface of the imaging substrate 19*e*, and the back substrate surface of the imaging substrate 19*e* faces against the back substrate surface of the illuminating substrate 19*f* across the plate portion 15*a* of the positioning unit 15. Further, the extending portion A1 passes through a notch (not shown) formed in the positioning unit 14. The extending portion A2 passes through each of notches (not shown) formed in the protruding portion 14*b* of the positioning unit 14 and the load receiving unit 17. The extending portion A3 passes through a notch (not shown) formed in the cylindrical structure of the load receiving unit 17, and the extending portion A4 passes through each of notches (not shown) formed in the open end portion of the load receiving unit 17 and the protruding portion 15*b* of the positioning unit 15, and the extending portion A5 passes through a notch (not shown) formed in the positioning unit 15.

Thereafter, the functional unit as mentioned above is arranged inside the capsule-like casing 2. The functional unit is inserted into the cylindrical trunk member 2*a*, and the optical domes 2*b* and 2*c* are attached respectively to the open ends on two sides of the cylindrical trunk member 2*a* in which the functional unit is housed. Each of the optical domes 2*b* and 2*c* is fixed to the inner circumferential surface of the cylindrical trunk member 2*a* near the open end and secured by a bonding agent or the like as shown in FIG. 1. Thus, the capsule endoscope 1 as shown in FIG. 1 is manufactured.

Figure 6:
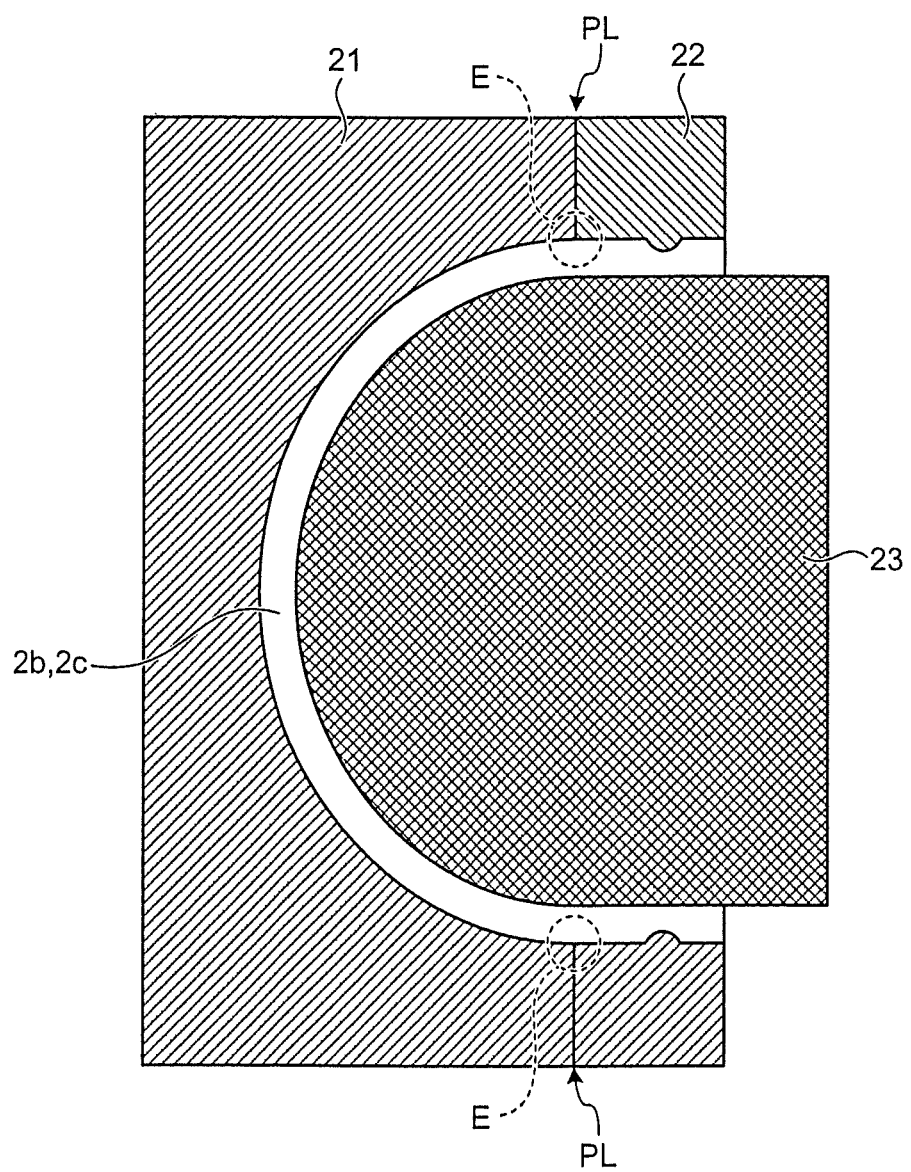
FIG. 6 is a schematic sectional view of an example of a mold for molding the optical dome.

Generation of burrs on the outer wall surfaces of the optical domes 2*b* and 2*c* will be described. FIG. 6 is a schematic sectional view of an example of a mold which is employed for molding the optical domes 2*b* and 2*c*. As shown in FIG. 6, the mold for molding the optical domes 2*b* and 2*c* are configured with a mold part 21 for molding an outer wall surface of a dome portion which forms a dome shape of the optical domes 2*b* and 2*c*, a mold part 22 for molding an outer circumferential surface of a cylindrical portion forming a cylindrical shape of the optical domes 2*b* and 2*c*, and a mold part 23 for molding an inner wall surface of the dome portion and the cylindrical portion of the optical domes 2*b* and 2*c*.

The dome portion of each of the optical domes 2*b* and 2*c* are subjected to mirror finish so that a clear intra-body image can be picked up through the optical domes 2*b* and 2*c*. Hence, a concave surface of the mold part 21 for molding the outer wall surface of the dome portion of each of the optical domes 2*b* and 2*c* must be subjected to polishing (mirror finish). Therefore, the mold part for molding the outer wall surface of each of the optical domes 2*b* and 2*c* is divided into the mold part 21 corresponding to a dome-portion side and the mold part 22 corresponding to a cylindrical-portion side, so as to secure a space for allowing the introduction of a blade or the like of a predetermined polisher close to the concave surface of the mold part 21. On the other hand, for the mirror finish of the dome portion of each of the optical domes 2*b* and 2*c*, a convex surface of the mold part 23 for molding the inner wall surface of the dome portion of each of the optical domes 2*b* and 2*c* is required to be polished. A dome-shape portion of the mold part 23, however, can be easily touched by the blade or the like of the polisher and it is not necessary to divide the mold part 23 as the mold parts 21 and 22 mentioned above.

Optically transparent resin material, glass material, or the like is injected into an internal space of the mold formed as a combination of the mold parts 21, 22, and 23 (i.e., a gap between the mold parts 21 and 22 and the mold part 23 shown in FIG. 6) by pressure, and the optical domes 2*b* and 2*c* of substantially uniform thickness are molded. The optical domes 2*b* and 2*c* thus molded by the mold each include an optically transparent dome portion whose inner wall surface and outer wall surface are mirror finished, and a cylindrical portion which smoothly leads to the open end of the dome portion and to whose outer circumferential surface the cylindrical trunk member 2*a* is fitted (see FIG. 1).

Here, the outer wall surface of each of the optical domes 2*b* and 2*c* is molded by the dome-portion side mold part 21 and the cylindrical-portion side mold part 22 as mentioned above. Hence, depending on a state of joint between the mold parts 21 and 22 (displacement, gap, and the like), a burr can be generated on the outer wall surface of each of the optical domes 2b and 2c. Specifically, the burr on the outer wall surface of each of the optical domes 2b and 2c is formed on the outer circumferential surface along a boundary between the joined mold parts 21 and 22, i.e., a parting line PL. In other words, the burr is formed in a boundary portion E of the outer wall surface of each of the optical domes 2b and 2c between the dome portion and the cylindrical portion.

Figure 7:
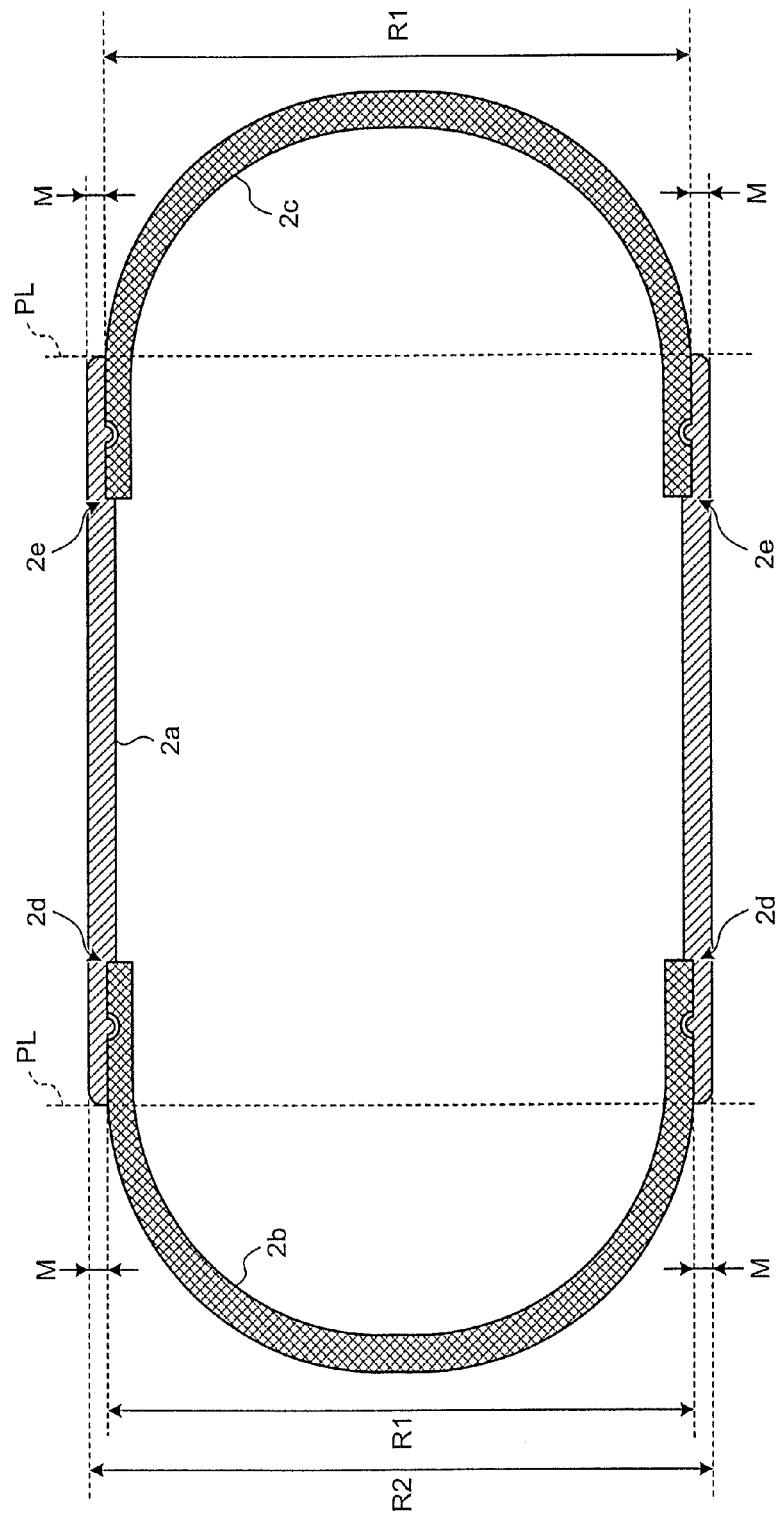
FIG. 7 is a schematic sectional view illustrating a state where the optical dome is fitted to each of open ends of a cylindrical trunk member.

A fitted state of the optical domes 2b and 2c thus formed by the mold and the cylindrical trunk member 2a will be described. FIG. 7 is a schematic sectional view illustrating a state of the optical domes 2b and 2c fitted to the two open ends of the cylindrical trunk member 2a. As shown in FIG. 7, the cylindrical trunk member 2a has an outer diameter dimension R2 which is larger than an outer diameter dimension R1 of the optical domes 2b and 2c formed in a substantially uniform thickness. The cylindrical trunk member 2a has such a cylindrical structure that the two open ends can be fitted to the outer circumferential surfaces of the cylindrical portions of the optical domes 2b and 2c. Further, the cylindrical trunk member 2a has steps 2d and 2e on the inner wall surfaces near the open ends. The steps 2d and 2e engage with the open ends of the cylindrical portions of the optical domes 2b and 2c, respectively. The steps 2d and 2e engage with the open ends of the optical domes 2b and 2c and thereby define the fitted position of the optical domes 2b and 2c.

Here, the cylindrical trunk member 2a covers the outer circumferential surfaces of the optical domes 2b and 2c up to a position corresponding to the parting line PL of the mold parts 21 and 22 mentioned above, in other words, up to a portion near the boundary portion E between the dome portion and the cylindrical portion of the optical domes 2b and 2c (see FIG. 6) when the optical domes 2b and 2c are fitted to the open ends. The cylindrical trunk member 2a thus covers the outer wall surfaces of the optical domes 2b and 2c up to a portion near the burrs formed on the optical domes 2b and 2c, and forms a step M higher than the burr on the outer wall surfaces of the optical domes 2b and 2c along the boundary portion E mentioned above. The cylindrical trunk member 2a can prevent the contact between the burr and the living body inside the subject by forming the step M near the burrs on the optical domes 2b and 2c.

Figure 8:
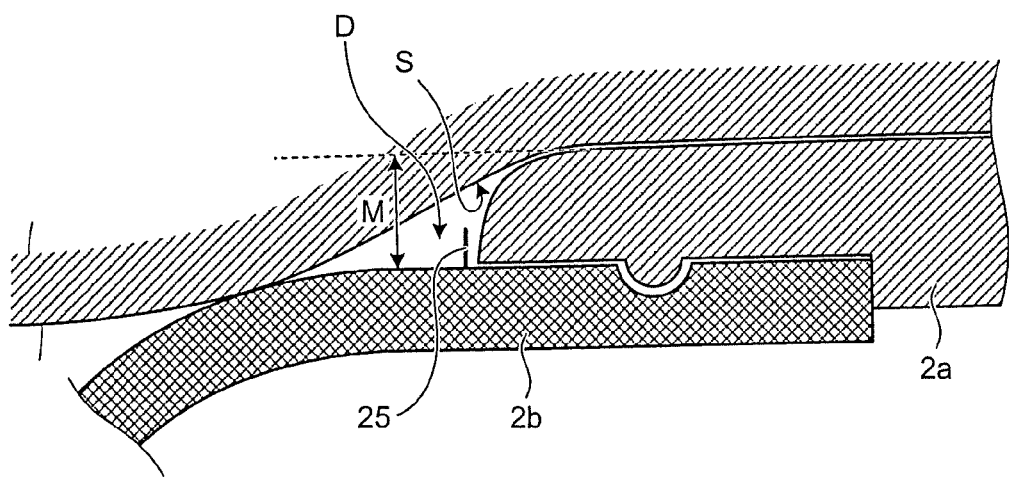
FIG. 8 is a schematic diagram for explaining a function of the cylindrical trunk member for avoiding a contact between a burr of the optical dome and a living body.

Specifically, when the capsule endoscope 1 (see FIG. 1) including the capsule-like casing 2 configured with the cylindrical trunk member 2a mentioned earlier and the optical domes 2b and 2c is introduced inside the subject, the cylindrical trunk member 2a forms a space D between an inner wall S of an internal organ inside the subject (an example of the living body) and the optical dome 2b by the step M formed on the outer wall surface of the optical dome 2b as shown in FIG. 8. The cylindrical trunk member 2a can maintain a separated state of a burr 25 of the optical dome 2b and the inner wall S of the internal organ by forming the space D with the step M. As a result, the contact between the burr 25 and the inner wall S of the internal organ can be prevented.

It is desirable that the outer peripheral edge of the open end of the cylindrical trunk member 2a is chamfered. The outer peripheral edge of the open end of the cylindrical trunk member 2a touches the living body (e.g., inner wall of the internal organ) while the capsule endoscope 1 moves inside the subject. When the outer peripheral edges of two open ends of the cylindrical trunk member 2a are chamfered, friction between the living body inside the subject and the cylindrical trunk member 2a can be reduced, and as a result, the capsule endoscope 1 can move inside the subject smoothly.

As can be seen from the above, in the first embodiment of the present invention, the capsule-like casing is formed with the cylindrical trunk member having a cylindrical structure with an outer diameter dimension larger than the outer diameter dimension of the optically transparent optical dome, and the open end of the cylindrical trunk member is fitted to the outer circumferential surface of the optical dome. The cylindrical trunk member covers the outer wall surface of the optical dome up to a portion near the burr formed in the optical dome, whereby a step higher than the height of the burr is formed near the burr. Therefore, when the living body inside the subject touches the capsule-like casing, the step between the optical dome and the cylindrical trunk member can form a space to allow prevention of contact between the burr on the optical dome and the living body. As a result, the burr of the optical dome and the living body inside the subject can be maintained in a separated state inside the subject, and the contact between the burr of the optical dome and the living body of the inside of the subject can be prevented.

In the capsule-type medical apparatus according to the present invention, even when the burr is formed on the optical dome, it is possible to prevent the living body from being hurt by the contact between the burr of the optical dome and the living body. In addition, since there is no need to perform a burr removal process for removing the burr on the optical dome after the molding process and the like of the optical dome, the work required for removing the burr can be eliminated. As a result, the manufacturing cost can be reduced, damages on the optical dome at the time of burr removal process can be prevented, and the manufacturing yield can be increased.

Further, in the first embodiment of the present invention, since the flexible substrate is employed as a circuit substrate such as the illuminating substrate, the imaging substrate, and the radio substrate, further reduction in size and weight can be made in comparison with the conventional capsule-type medical apparatus employing the rigid substrate as the circuit substrate, and the reduction in substrate cost can be realized.

Second Embodiment

A second embodiment of the present invention will be described. In the first embodiment mentioned above, the cylindrical trunk member 2a covering the outer wall surface of the optical domes 2b and 2c up to a portion near the burr forms a step higher than the burr, so as to prevent the contact between the living body of the inside of the subject and the burr of the optical dome. In the second embodiment, the cylindrical trunk member is fitted to the optical dome in such a manner that the burr is housed (covered) in a space between the inner wall surface of the cylindrical trunk member and the outer wall surface of the optical dome, whereby the contact between the living body inside the subject and the burr of the optical dome is prevented.

Figure 9:
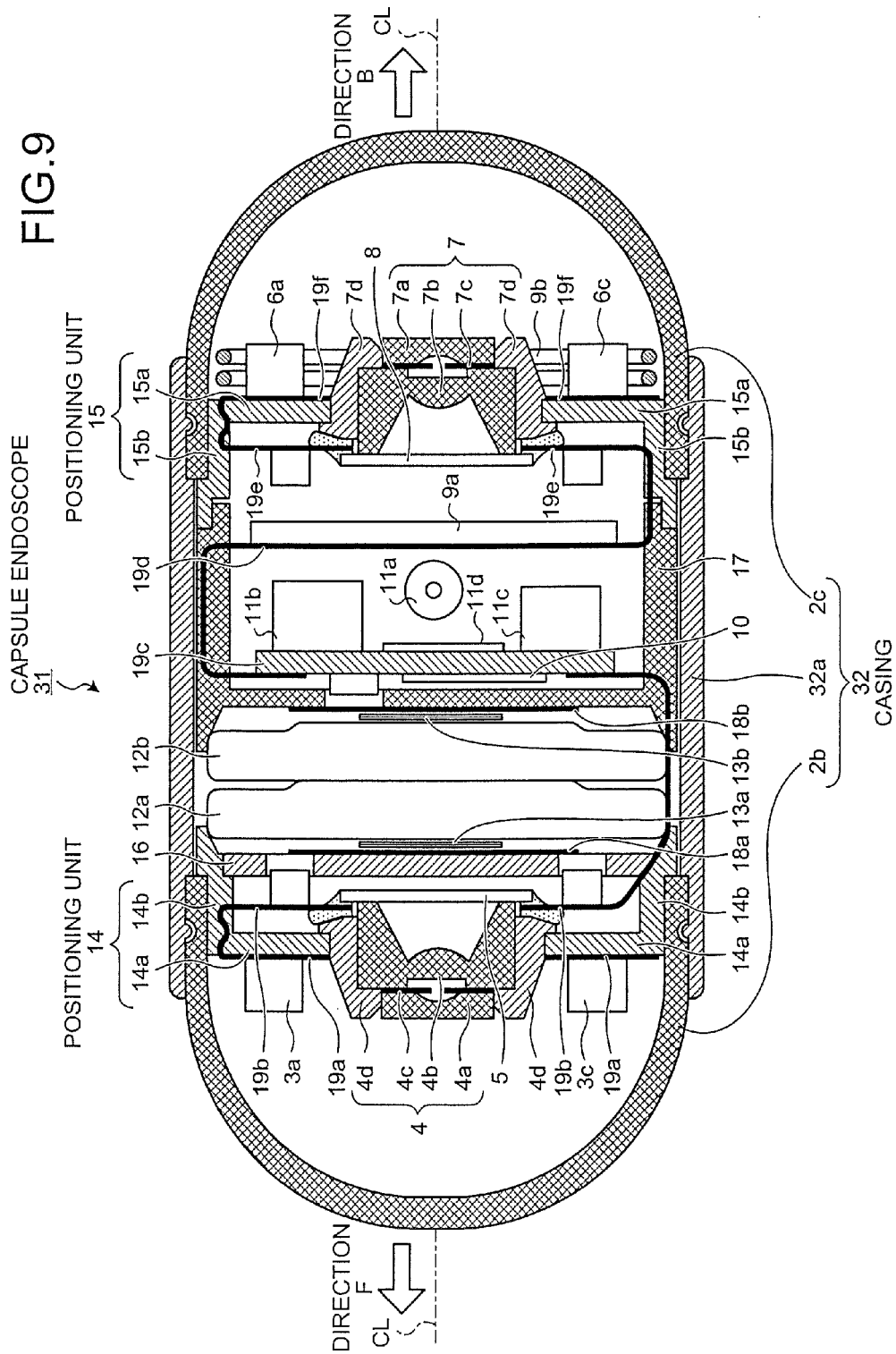
FIG. 9 is a schematic sectional view of one configuration example of a capsule endoscope according to a second embodiment of the present invention.

FIG. 9 is a schematic sectional view of one configuration example of a capsule endoscope according to the second embodiment of the present invention. As shown in FIG. 9, a capsule endoscope 31 according to the second embodiment includes a casing 32 in place of the casing 2 of the capsule endoscope 1 according to the first embodiment described above. The casing 32 is a capsule-like casing easily introduced inside the internal organ of the subject similarly to the casing 2 mentioned earlier. The casing 32 includes a cylindrical trunk member 32a in place of the cylindrical trunk member 2a of the casing 2 mentioned above. In other respects, the configuration of the capsule endoscope of the second embodiment is the same as that of the first embodiment, and the same components are denoted by the same reference characters.

Figure 10:
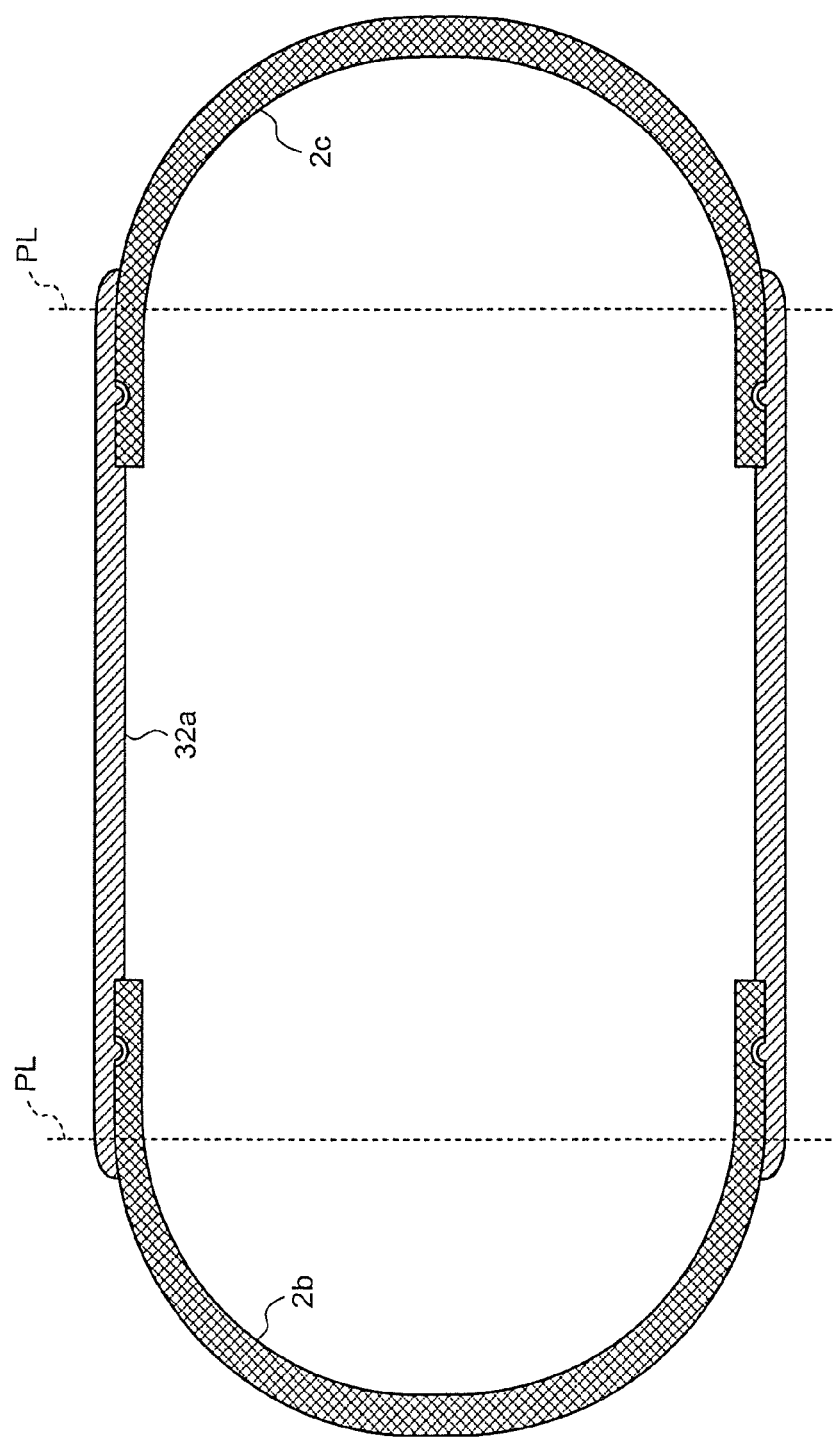
FIG. 10 is a schematic sectional view illustrating a state where the cylindrical trunk member and the optical dome are fitted with each other so that the burr formed on the optical dome is covered.

FIG. 10 is a schematic sectional view illustrating a state of the cylindrical trunk member 32a and the optical domes 2b and 2c fitted to each other in such a manner that the burrs formed on the optical domes 2b and 2c are covered. As shown in FIG. 10, the optical domes 2b and 2c are fitted to the inner circumferential surface of the cylindrical trunk member 32a near the open ends thereof in such a manner that the cylindrical trunk member 32a covers the outer circumferential surface of each of the optical domes 2b and 2c so as to extend over a portion corresponding to the parting line PL, in other words, in such a manner that the cylindrical trunk member 32a covers the boundary E (see FIG. 6) between the dome portion and the cylindrical portion of each of the optical domes 2b and 2c and extends further to the dome-portion side. The cylindrical trunk member 32a is fitted to the optical domes 2b and 2c and at the same time covers the burrs on the optical domes 2b and 2c. The burrs on the optical domes 2b and 2c are housed between the inner wall surface of the cylindrical trunk member 32a and the outer wall surfaces of the optical domes 2b and 2c. Functions and structures of the cylindrical trunk member 32a other than those mentioned above are the same as those of the cylindrical trunk member 2a of the capsule endoscope 1 according to the first embodiment mentioned above.

Figure 11:
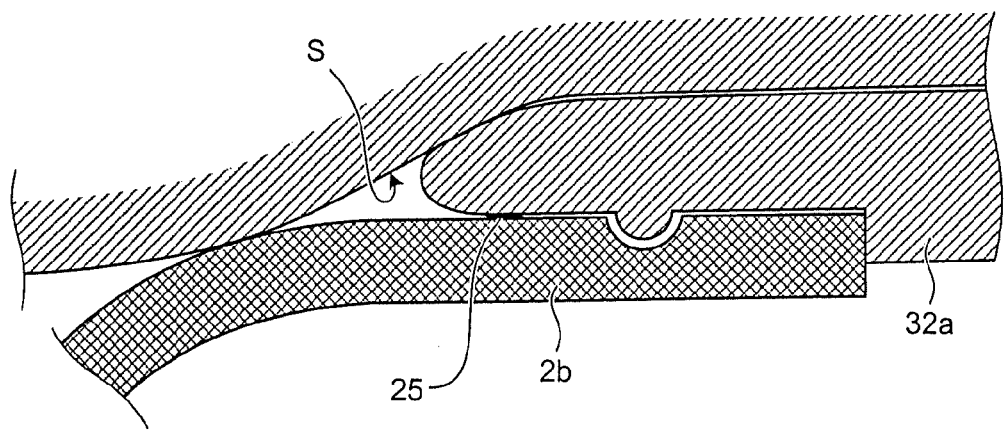
FIG. 11 is a schematic diagram illustrating a state where the contact between the burr and the living body is avoided by the cylindrical trunk member covering the burr of the optical dome.

When the capsule endoscope 31 (see FIG. 9) having the capsule-like casing 32 configured with the cylindrical trunk member 32a and the optical domes 2b and 2c is introduced inside the subject, the cylindrical trunk member 32a is in such a state that it covers (houses) the burr 25 on the optical dome 2b on the inner circumferential surface side as shown in FIG. 11, for example, and thus, the cylindrical trunk member 32a can prevent the contact between the burr 25 of the optical dome 2b and the inner wall S of the internal organ.

It is desirable that the outer peripheral edges of the open ends of the cylindrical trunk member 32a are chamfered as shown in FIGS. 10 and 11, for example. The outer peripheral edge of the open end of the cylindrical trunk member 32a touches the living body (e.g., inner wall of the internal organ) while the capsule endoscope 31 moves inside the subject. When the outer peripheral edge of the open end of the cylindrical trunk member 32a is chamfered, friction between the living body inside the subject and the cylindrical trunk member 32a can be reduced, and as a result, the capsule endoscope 31 can move inside the subject smoothly.

As described above, in the second embodiment of the present invention, the cylindrical trunk member is fitted to the outer circumferential surface of the optical dome, and the burr of the optical domes is covered in such a manner that the burr is housed between the inner circumferential surface of the cylindrical trunk member and the outer circumferential surface of the optical dome. In other respects, the second embodiment is configured similarly to the first embodiment. Hence, the second embodiment can obtain the same advantageous effects as those obtained in the first embodiment, and further, though the step higher than the burr of the optical dome is not formed on the outer circumferential surface of the optical dome, the contact between the burr of the optical dome and the living body inside the subject can be securely prevented in the subject.

Further, since it is not necessary to make the step, which is formed between the optical dome and the cylindrical trunk member when the cylindrical trunk member is fitted to the outer circumferential surface of the optical dome, higher than the burr of the optical dome, the thickness of the cylindrical trunk member can be made as thin as possible. As a result, the size of the capsule-like casing configured with one or more optical domes and the cylindrical trunk member can be further reduced.

In the first and the second embodiments of the present invention described above, the thickness of the optical domes 2b and 2c are made substantially uniform. The thickness of the optical dome is not limited thereto, and can be non-uniform. For example, the step that engages with the open end of the cylindrical trunk member may be formed on the outer wall surface of the optical dome. Such structure can be adopted in the first embodiment as far as a step higher than the burr of the optical dome is formed near the burr by the cylindrical trunk member to which the optical dome is fitted.

Further, in the first and the second embodiments of the present invention described above, a capsule endoscope which has the imaging function and the radio communication function to obtain an intra-body image as an example of the in-vivo information is described as the capsule-type medical apparatus introduced inside the subject. The capsule-type medical apparatus is not limited to the capsule endoscope, however. For example, the capsule-type medical apparatus can be a capsule-type pH measurement device which measures pH information inside the living body as the in-vivo information, a capsule-type drug administration device which has a function of spraying or injecting a drug inside the living body, a capsule-type collecting device which collects a material (such as a body tissue) in the living body as the in-vivo information, and the like.

The capsule-type medical apparatus according to the present invention has a capsule-like casing configured with a cylindrical trunk member having a cylindrical structure with an outer diameter dimension larger than the outer diameter dimension of an optically transparent optical dome and an open end of the cylindrical trunk member is fitted to the outer circumferential surface of the optical dome. The cylindrical trunk member covers the outer wall surface of the optical dome up to a portion near the burr formed on the optical dome so as to form a step higher than the burr near the burr. Thus, when the living body inside the subject touches the capsule-like casing, the step between the optical dome and the cylindrical trunk member can form a space to avoid the contact between the burr of the optical dome and the living body. As a result, the burr of the optical dome and the living body inside the subject can be maintained in a separated state inside the subject, and the contact between the burr of the optical dome and the living body inside the subject can be prevented.

Further, the capsule-type medical apparatus according to the present invention has a capsule-like casing configured with a cylindrical trunk member having a cylindrical structure with an outer diameter dimension larger than the outer diameter dimension of the optically transparent optical dome, and the open end of the cylindrical trunk member is fitted to the outer circumferential surface of the optical dome so that the cylindrical trunk member covers the burr on the optical dome and the optical dome itself. Thus, when the living body inside the subject touches the capsule-like casing, the contact between the burr of the optical dome and the living body can be securely prevented.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

INDUSTRIAL APPLICABILITY

As can be seen from the foregoing, the capsule-type medical apparatus and the method of manufacturing the capsule-type medical apparatus according to the present invention are useful for capsule-type medical apparatuses introduced inside the subject, and more particularly are suitable for a capsule-type medical apparatus and a method of manufacturing a capsule-type medical apparatus which can prevent the contact between a burr formed on the optical dome which is a part of the capsule-like casing and a living body inside the subject.

What is claimed is:

1. A capsule-type medical apparatus comprising a capsule-like casing and configured to be introduced inside a subject,
the capsule-like casing, comprising:
an optical dome that forms a transparent portion of the capsule-like casing; and
a cylindrical trunk member that forms a trunk portion of the capsule-like casing,
the cylindrical trunk member being fitted onto an outer circumferential surface of the optical dome and preventing a contact between a living body in the subject and a burr formed on the optical dome; wherein
the cylindrical trunk member is fitted onto an outer circumferential surface of the optical dome, and covers the burr on the optical dome in such a manner that the burr is housed between an outer circumferential surface of the optical dome and an inner circumferential surface of the cylindrical trunk member to prevent the contact between the living body in the subject and the burr.

2. The capsule-type medical apparatus according to claim 1, wherein the optical dome is formed in a uniform thickness.

3. The capsule-type medical apparatus according to claim 1, wherein
the optical dome is configured with
an optically transparent dome portion, and
a cylindrical portion leading to an open end of the dome portion and having an outer circumferential surface on which the cylindrical trunk member is fitted, and
the burr is formed on a boundary between the dome portion and the cylindrical portion.

4. The capsule-type medical apparatus according to claim 3, wherein an outer surface and an inner surface of the dome portion are mirror finished.

5. The capsule-type medical apparatus according to claim 1, wherein the cylindrical trunk member has an outer peripheral edge of an open end fitted onto the outer circumferential surface of the optical dome, the peripheral edge being chamfered.

6. The capsule-type medical apparatus according to claim 1, wherein the cylindrical trunk member has an open end on each of two sides, and each of the open ends is fitted onto the outer circumferential surface of the optical dome.

* * * * *